United States Patent
Stahl et al.

(10) Patent No.: US 12,306,184 B2
(45) Date of Patent: May 20, 2025

(54) BIOMARKERS OF MEMBRANOUS GLOMERULONEPHRITIS

(71) Applicant: EUROIMMUN Medizinische Labordiagnostika AG, Luebeck (DE)

(72) Inventors: Rolf Stahl, Hamburg (DE); Elion Hoxha, Hamburg (DE); Linda Reinhard, Hamburg (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 0 days.

(21) Appl. No.: 18/046,496

(22) Filed: Oct. 13, 2022

(65) Prior Publication Data
US 2023/0133318 A1 May 4, 2023

(30) Foreign Application Priority Data
Oct. 14, 2021 (EP) .................................... 21202650

(51) Int. Cl.
*G01N 33/564* (2006.01)
(52) U.S. Cl.
CPC . *G01N 33/564* (2013.01); *G01N 2333/70503* (2013.01); *G01N 2800/347* (2013.01); *G01N 2800/52* (2013.01)
(58) Field of Classification Search
CPC ....... G01N 33/564; G01N 2333/70503; G01N 2800/347; G01N 2800/52
See application file for complete search history.

(56) References Cited

U.S. PATENT DOCUMENTS

2006/0035826 A1   2/2006  Lin et al.
2021/0309729 A1*  10/2021 Cukierman .......... C07K 14/475

FOREIGN PATENT DOCUMENTS

| EP | 2977758 | | 1/2016 | |
|---|---|---|---|---|
| EP | 2977758 | A1 * | 1/2016 | ......... A61K 38/1709 |
| WO | 2017/009245 | | 1/2017 | |
| WO | 2021/023816 | | 2/2021 | |

OTHER PUBLICATIONS

Niimi et al., "Monoclonal antibodies discriminating netrin-G1 and netrin-G2 neuronal pathways", Journal of Neuroimmunology, vol. 192, 2007, pp. 99-104. IDS filed on Dec. 20, 2022 (Year: 2007).*
Basnakian, Alexei G. "Netrin-1: a potential universal biomarker for acute kidney injury." American journal of physiology. Renal physiology vol. 294,4 (2008): F729-30. doi:10.1152/ajprenal.00085.2008 (Year: 2008).*
Niimi et al., "Monoclonal antibodies discriminating netrin-G1 and netrin-G2 neuronal pathways", Journal of Neuroimmunology, vol. 192, 2007, pp. 99-104.
Hanna D. Zane, "Immunology: Theoretical & Practical Concepts in Laboratory Medicine", Philadelphia, Pa, W.B. Saunders Company, 2001, pp. 149 and 185.
Reinhard et al., "Netrin G1 Is a Novel Target Antigen in Membranous Nephropathy", American Society of Nephrology, Kidney Week Abstract: PO1468 Nov. 4, 2021, 3 pages.

* cited by examiner

*Primary Examiner* — Gregory S Emch
*Assistant Examiner* — McKenzie A Dunn
(74) *Attorney, Agent, or Firm* — Grüneberg and Myers PLLC

(57) ABSTRACT

Netrin G1 is disclosed as a biomarker of membranous glomerulonephritis (MGN). Netrin G1 antigen-comprising polypeptides and Netrin G1 antibodies can be used in in vitro methods and kits for diagnosis, prognosis and monitoring of MGN of patients with circulating Netrin G1 autoantibodies.

17 Claims, 5 Drawing Sheets
Specification includes a Sequence Listing.

PLA2R1-antibody positive patient serum

MGN Index Patient

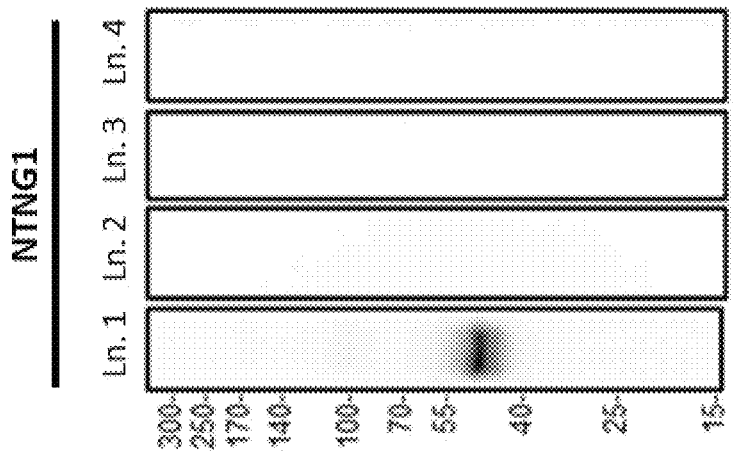
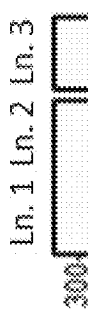
FIG. 4A
FIG. 4B

IHC: NTNG in MGN index patient

```
                              SEQUENCE LISTING

Sequence total quantity: 10
SEQ ID NO: 1            moltype = AA  length = 539
FEATURE                 Location/Qualifiers
source                  1..539
                        mol_type = protein
                        organism = Homo sapiens
SEQUENCE: 1
MYLSRFLSIH ALWVTVSSVM QPYPLVWGHY DLCKTQIYTE EGKVWDYMAC QPESTDMTKY   60
LKVKLDPPDI TCGDPPETFC AMGNPYMCNN ECDASTPELA HPPELMFDFE GRHPSTFWQS  120
ATWKEYPKPL QVNITLSWSK TIELTDNIVI TFESGRPDQM ILEKSLDYGR TWQPYQYYAT  180
DCLDAFHMDP KSVKDLSQHT VLEIICTEEY STGYTTNSKI IHFEIKDRFA FFAGPRLRNM  240
ASLYGQLDTT KKLRDFFTVT DLRIRLLRPA VGEIFVDELH LARYFYAISD IKVRGRCKCN  300
LHATVCVYDN SKLTCECEHN TTGPDCGKCK KNYQGRPWSP GSYLPIPKGT ANTCIPSISS  360
IGNCECFGHS NRCSYIDLLN TVICVSCKHN TRGQHCELCR LGYFRNASAQ LDDENVCIEC  420
YCNPLGSIHD RCNGSGFCEC KTGTTGPKCD ECLPGNSWHY GCQPNVCDNE LLHCQNGGTC  480
HNNVRCLCPA AYTGILCEKL RCEEAGSCGS DSGQGAPPHG SPALLLLTTL LGTASPLVF   539

SEQ ID NO: 2            moltype = AA  length = 510
FEATURE                 Location/Qualifiers
source                  1..510
                        mol_type = protein
                        organism = Homo sapiens
SEQUENCE: 2
MYLSRFLSIH ALWVTVSSVM QPYPLVWGHY DLCKTQIYTE EGKVWDYMAC QPESTDMTKY   60
LKVKLDPPDI TCGDPPETFC AMGNPYMCNN ECDASTPELA HPPELMFDFE GRHPSTFWQS  120
ATWKEYPKPL QVNITLSWSK TIELTDNIVI TFESGRPDQM ILEKSLDYGR TWQPYQYYAT  180
DCLDAFHMDP KSVKDLSQHT VLEIICTEEY STGYTTNSKI IHFEIKDRFA FFAGPRLRNM  240
ASLYGQLDTT KKLRDFFTVT DLRIRLLRPA VGEIFVDELH LARYFYAISD IKVRGRCKCN  300
LHATVCVYDN SKLTCECEHN TTGPDCGKCK KNYQGRPWSP GSYLPIPKGT ANTCIPSISS  360
IGNCECFGHS NRCSYIDLLN TVICVSCKHN TRGQHCELCR LGYFRNASAQ LDDENVCIEC  420
YCNPLGSIHD RCNGSGFCEC KTGTTGPKCD ECLPGNSWHY GCQPNVCDNE LLHCQNGGTC  480
HNNVRCLCPA AYTGILCEKL RCEEAGSCGS                                   510

SEQ ID NO: 3            moltype = AA  length = 482
FEATURE                 Location/Qualifiers
source                  1..482
                        mol_type = protein
                        organism = Homo sapiens
SEQUENCE: 3
HYDLCKTQIY TEEGKVWDYM ACQPESTDMT KYLKVKLDPP DITCGDPPET FCAMGNPYMC   60
NNECDASTPE LAHPPELMFD FEGRHPSTFW QSATWKEYPK PLQVNITLSW SKTIELTDNI  120
VITFESGRPD QMILEKSLDY GRTWQPYQYY ATDCLDAFHM DPKSVKDLSQ HTVLEIICTE  180
EYSTGYTTNS KIIHFEIKDR FAFFAGPRLR NMASLYGQLD TTKKLRDFFT VTDLRIRLLR  240
PAVGEIFVDE LHLARYFYAI SDIKVRGRCK CNLHATVCVY DNSKLTCECE HNTTGPDCGK  300
CKKNYQGRPW SPGSYLPIPK GTANTCIPSI SSIGNCECFG HSNRCSYIDL LNTVICVSCK  360
```

-continued

```
HNTRGQHCEL CRLGYFRNAS AQLDDENVCI ECYCNPLGSI HDRCNGSGFC ECKTGTTGPK    420
CDECLPGNSW HYGCQPNVCD NELLHCQNGG TCHNNVRCLC PAAYTGILCE KLRCEEAGSC    480
GS                                                                  482

SEQ ID NO: 4              moltype = DNA   length = 1620
FEATURE                   Location/Qualifiers
source                    1..1620
                          mol_type = unassigned DNA
                          organism = Homo sapiens
SEQUENCE: 4
atgtatttgt caagattcct gtcgattcat gcccttgggg ttacggtgtc ctcagtgatg     60
cagccctacc ctttggtttg gggacattat gatttgtgta agactcagat ttacacggaa    120
gaagggaaag tttgggatta catggcctgc cagccggaat ccacggacat gacaaaatat    180
ctgaaagtga aactcgatcc tccggatatt acctgtggaa accctcctga cgagttctgt    240
gcaatgggca atcctacat gtgcaataat gagtgtgatg cgagtacccc tgagctggca    300
cacccccctg agctgatgtt tgattttgaa ggaagacatc cctccacatt ttggcagtct    360
gccacttgga aggagtatcc caagcctctc aggttaaca tcactctgtc ttggagcaaa    420
accattgagc taacagacaa catagttatt acctttgaat ctggacgtcc agaccaaatg    480
atcctggaga agtctctcga ttatggacga acatggcagc cctatcagta ttatgccaca    540
gactgcttag atgcttttca catggatcct aaatccgtga aggatttatc acagcatacg    600
gtcttagaaa tcatttgcac agaagagtac tcaacagggt atacaacaaa tagcaaaata    660
atccactttg aaatcaaaga caggttcgcg ttttttgctg gacctcgcct acgcaatatg    720
gcttccctct acggacagct ggatacaacc aagaaactca gagatttctt tacagtcaca    780
gacctgagga taaggctgtt aagaccagcc gttgggaaa tatttgtaga tgagctacac    840
ttggcacgct acttttacgc gatctcagac ataaaggtgc gaggaaggtg caagtgtaat    900
ctccatgcca ctgtatgtgt gtatgacaac agcaaattga catgcgaatg tgagcacaac    960
actacaggtc cagactgtgg gaaatgcaag aagaattatc agggccgacc ttggagtcca   1020
ggctcctatc tccccatccc caaggcact gcaaatacc gtatcccag tatttccagt    1080
attggtaatt gtgaatgctt cggccactcc aatcgatgca gttatatcga tctgctaaat    1140
acagtcattt gcgtgagctg taaacacaac actagagggc agcactgtga gttatgcagg    1200
ctgggctact tcagaaatgc ttctgcacaa ctggacgatg agaatgtgtg catagagtgt    1260
tattgtaacc ctttgggctc aatccatgat cgttgtaatg gctcaggatt tgtgagtgt    1320
aagactggaa caacagggcc taagtgtgat gagtgtctgc cgggaaattc ctggcactac    1380
ggctgtcaac cgaatgtctg cgacaacgag ctccctgcact gccacaacgg agggacgtgc    1440
cacaacaacg tgcgctgcct gtgcccggcc gcatacacgg gcatcctctg cgagaagctg    1500
cggtgcgagg aggctggcag ctgcggctcc gactctggcc agggcgcgcc ccgcacggc     1560
tccccagcgc tgctgctgct gaccacgctg ctgggaaccg ccagccccct ggtgttctag    1620

SEQ ID NO: 5              moltype = AA    length = 438
FEATURE                   Location/Qualifiers
source                    1..438
                          mol_type = protein
                          organism = Homo sapiens
SEQUENCE: 5
MYLSRFLSIH ALWVTVSSVM QPYPLVWGHY DLCKTQIYTE EGKVWDYMAC QPESTDMTKY     60
LKVKLDPPDI TCGDPPETFC AMGNPYMCNN ECDASTPELA HPPELMFDFE GRHPSTFWQS    120
ATWKEYPKPL QVNITLSWSK TIELTDNIVI TFESGRPDQM ILEKSLDYGR TWQPYQYYAT    180
DCLDAFHMDP KSVKDLSQHT VLEIICTEEY STGYTTNSKI IHFEIKDRFA FFAGPRLRNM    240
ASLYGQLDTT KKLRDFFTVT DLRIRLLRPA VGEIFVDELH LARYFYAISD IKVRGRCKCN    300
LHATVCVYDN SKLTCECEHN TTGPDCGKCK KNYQGRPWSP GSYLPIPKGT ANTCIPSISS    360
IGTNVCDNEL LHCQNGGTCH NNVRCLCPAA YTGILCEKLR CEEAGSCGSD SGQGAPPHGS    420
PALLLLTTLL GTASPLVF                                                  438

SEQ ID NO: 6              moltype = AA    length = 364
FEATURE                   Location/Qualifiers
source                    1..364
                          mol_type = protein
                          organism = Homo sapiens
SEQUENCE: 6
MYLSRFLSIH ALWVTVSSVM QPYPLVWGHY DLCKTQIYTE EGKVWDYMAC QPESTDMTKY     60
LKVKLDPPDI TCGDPPETFC AMGNPYMCNN ECDASTPELA HPPELMFDFE GRHPSTFWQS    120
ATWKEYPKPL QVNITLSWSK TIELTDNIVI TFESGRPDQM ILEKSLDYGR TWQPYQYYAT    180
DCLDAFHMDP KSVKDLSQHT VLEIICTEEY STGYTTNSKI IHFEIKDRFA FFAGPRLRNM    240
ASLYGQLDTT KKLRDFFTVT DLRIRLLRPA VGEIFVDELH LARYFYAISD IKVRGRCKCN    300
LHATVCVYDN SKLTCECEHN TTGPDCGKCK KNYQGRPWSP GSYLPIPKGT ANTCIPSISS    360
IGSK                                                                 364

SEQ ID NO: 7              moltype = AA    length = 480
FEATURE                   Location/Qualifiers
source                    1..480
                          mol_type = protein
                          organism = Homo sapiens
SEQUENCE: 7
MYLSRFLSIH ALWVTVSSVM QPYPLVWGHY DLCKTQIYTE EGKVWDYMAC QPESTDMTKY     60
LKVKLDPPDI TCGDPPETFC AMGNPYMCNN ECDASTPELA HPPELMFDFE GRHPSTFWQS    120
ATWKEYPKPL QVNITLSWSK TIELTDNIVI TFESGRPDQM ILEKSLDYGR TWQPYQYYAT    180
DCLDAFHMDP KSVKDLSQHT VLEIICTEEY STGYTTNSKI IHFEIKDRFA FFAGPRLRNM    240
ASLYGQLDTT KKLRDFFTVT DLRIRLLRPA VGEIFVDELH LARYFYAISD IKVRGRCKCN    300
LHATVCVYDN SKLTCECEHN TTGPDCGKCK KNYQGRPWSP GSYLPIPKGT ANTCIPSISS    360
```

```
IGNPPKFNRI WPNISSLEVS NPKQVAPKLA LSTVSSVQVA NHKRANVCDN ELLHCQNGGT    420
CHNNVRCLCP AAYTGILCEK LRCEEAGSCG SDSGQGAPPH GSPALLLLTT LLGTASPLVF    480

SEQ ID NO: 8            moltype = AA  length = 460
FEATURE                 Location/Qualifiers
source                  1..460
                        mol_type = protein
                        organism = Homo sapiens
SEQUENCE: 8
MYLSRFLSIH ALWVTVSSVM QPYPLVWGHY DLCKTQIYTE EGKVWDYMAC QPESTDMTKY     60
LKVKLDPPDI TCGDPPETFC AMGNPYMCNN ECDASTPELA HPPELMFDFE GRHPSTFWQS    120
ATWKEYPKPL QVNITLSWSK TIELTDNIVI TFESGRPDQM ILEKSLDYGR TWQPYQYYAT    180
DCLDAFHMDP KSVKDLSQHT VLEIICTEEY STGYTTNSKI IHFEIKDRFA FFAGPRLRNM    240
ASLYGQLDTT KKLRDFFTVT DLRIRLLRPA VGEIFVDELH LARYFYAISD IKVRGRCKCN    300
LHATVCVYDN SKLTCECEHN TTGPDCGKCK KNYQGRPWSP GSYLPIPKGT ANTCIPSISS    360
IGNPPKFNRI WPNISSLEVS NPKQANVCDN ELLHCQNGGT CHNNVRCLCP AAYTGILCEK    420
LRCEEAGSCG SDSGQGAPPH GSPALLLLTT LLGTASPLVF                          460

SEQ ID NO: 9            moltype = AA  length = 1462
FEATURE                 Location/Qualifiers
source                  1..1462
                        mol_type = protein
                        organism = Homo sapiens
SEQUENCE: 9
MLLSPSLLLL LLLGAPRGCA EGVAAALTPE RLLEWQDKGI FVIQSESLKK CIQAGKSVLT     60
LENCKQANKH MLWKWVSNHG LFNIGGSGCL GLNFSAPEQP LSLYECDSTL VSLRWRCNRK    120
MITGPLQYSV QVAHDNTVVA SRKYIHKWIS YGSGGGDICE YLHKDLHTIK GNTHGMPCMF    180
PPQYNHQWHH ECTREGREDD LLWCATTSRY ERDEKWGFCP DPTSAEVGCD TIWEKDLNSH    240
ICYQFNLLSS LSWSEAHSSC QMQGGTLLSI TDETEENFIR EHMSSKTVEV WMGLNQLDEH    300
AGWQWSDGTP LNYLNWSPEV NFEPPVEDHC GTFSSFMPSA WRSRDCESTL PYICKKYLNH    360
IDHEIVEKDA WKYYATHCEP GWNPYNRNCY KLQKEEKTWH EALRSCQADN SALIDITSLA    420
EVEFLVTLLG DENASETWIG LSSNKIPVSF EWSNDSSVIF TNWHTLEPHI FPNRSQLCVS    480
AEQSEGHWKV KNCEERLFYI CKKAGHVLSD AESGCQEGWE RHGGFCYKID TVLRSFDQAS    540
SGYYCPPALV TITNRFEQAF ITSLISSVVK MKDSYFWIAL QDQNDTGEYT WKPVGQKPEP    600
VQYTHWNTHQ PRYSGGCVAM RGRHPLGRWE VKHCRHFKAM SLCKQPVENQ EKAEYEERWP    660
FHPCYLDWES EPGLASCFKV FHSEKVLMKR TWREAEAFCE EFGAHLASFA HIEEEENFVNE   720
LLHSKFNWTE ERQFWIGFNK RNPLNAGSWE WSDRTPVVSS FLDNTYFGED ARNCAVYKAN    780
KTLLPLHCGS KREWICKIPR DVKPKIPFWY QYDVPWLFYQ DAEYLFHTFA SEWLNFEFVC    840
SWLHSDLLTI HSAHEQEFIH SKIKALSKYG ASWWIGLQEE RANDEFRWRD GTPVIYQNWD    900
TGRERTVNNQ SQRCGFISSI TGLWGSEECS VSMPSICKRK KVWLIEKKKD TPKQHGTCPK    960
WLYFNYKCLL LNIPKDPSSW KNWTHAQHFC AEEGGTLVAI ESEVEQAFIT MNLFGQTTSV   1020
WIGLQNDDYE TWLNGKPVVY SNWSPFDIIN IPSHNTTEVQ KHIPLCALLS SNPNFHFTGK   1080
WYFEDCGKEG YGFVCEKMQD TSGHGVNTSD MYPMPNTLEV GNRTYKIINA NMTWYAAIKT   1140
CLMHKAQLVS ITDQYHQSFL TVVLNRLGYA HWIGLFTTDN GLNFDWSDGT KSSFTFWKDE   1200
ESSLLGDCVF ADSNGRWHST ACESFLQGAI CHVPPETRQS EHPELCSETS IPWIKFKSNC   1260
YSFSTVLDSM SFEAAHEFCK KEGSNLLTIK DEAENAFLLE ELFAFGSSVQ MVWLNAQFDG   1320
NNETIKWFDG TPTDQSNWGI RKPDTDYFKP HHCVALRIPE GLWQLSPCQE KKGFICKMEA   1380
DIHTAEALPE KGPSHSIIPL AVVLTLIVIV AICTLSFCIY KHNGGFFRRL AGFRNPYYPA   1440
TNFSTVYLEE NILISDLEKS DQ                                            1462

SEQ ID NO: 10           moltype = AA  length = 1656
FEATURE                 Location/Qualifiers
source                  1..1656
                        mol_type = protein
                        organism = Homo sapiens
SEQUENCE: 10
MGLQARRWAS GSRGAAGPRR GVLQLLPLPL PLPLLLLLLL RPGAGRAAAQ GEAEAPTLYL     60
WKTGPWGRCM GDECGPGGIQ TRAVWCAHVE GWTTLHTNCK QAERPNNQQN CFKVCDWHKE    120
LYDWRLGPWN QCQPVISKSL EKPLECIKGE GIQVREIAC IQKDKDIPAE DIICEYFEPK    180
PLLEQACLIP CQQDCIVSEF SAWSECSKTC GSGLQHRTRH VVAPPQFGGS GCPNLTEFQV    240
CQSSPCEAEE LRYSLHVGPW STCSMPHSRQ VRQARRRGKN KEREKDRSKG VKDPEARELI    300
KKKRNRNRQN RQENKYWDIQ IGYQTREVMC INKTGKAADL SFCQQEKLPM TFQSCVITKE    360
CQVSEWSEWS PCSKTCHDMV SPAGTRVRTR TIRQFPIGSE KECPEFEEKE PCLSQGDGVV    420
PCATYGWRTT EWTECRVDPL LSQQDKRRGN QTALCGGGIQ TREVYCVQAN ENLLSQLSTH    480
KNKEASKPMD LKLCTGPIPN TTQLCHIPCP TECECVSPWSA WGPCTYENCN DQQGKKGFKL    540
RKRRITNEPT GGSGVTGNCP HLLEAIPCEE PACYDWKAVR LGNCEPDNGK ECGPGTQVQE    600
VVCINSDGEE VDRQLCRDAI FPIPVACDAP CPKDCVLSTW STWSSCSHTC SGKTTEGKQI    660
RARSILAYAG EEGGIRCPNS SALQEVRSCN EHPCTVYHWQ TGPWGQCIED TSVSSFNTTT    720
TWNGEASCSV GMQTRKVICV RVNVGQVGPK KCPESLRPET VRPCLLPCKK DCIVTPYSDW    780
TSCPSSCKEG DSSIRKQSRH RVIIQLPANG GRDCTDPLYE EKACEAPQAC QSYRWKTHKW    840
RRCQLVPWSV QQDSPGAQEG CGPGRQARAI TCRKQDGGQA GIHECLQYAG PVPALTQACQ    900
IPCQDDCQLT SWSKFSSCNG DCGAVRTRKR TLVGKSKKKE KCKNSHLYPL IETQYCPCDK    960
YNAQPVGNWS DCILPEGKVE VLLGMKVQGD IKECGQGYRY QAMACYDGNG RLVETSRCNS   1020
GYIEEACIIP CPSDCKLSEW SNWSRCSKSC GSGVKVRSKW LREKPYNGGR PCPKLDHVNQ   1080
AQVYEVVPCH SDCNQYLWVT EPWSICKVTF VNMRENCGEG VQTRKVRCMQ NTADGPSEHV   1140
EDYLCDPEEM PLGSRVCKLP CPEDCVISEW GPWTQCVLPC NQSSFRQRSA DPIRQPADEG   1200
RSCPNAVEKE PCNLNKNCYH YDYNVTDWST CQLSEKAVCG NGIKTRMLDC VRSDGKSVDL   1260
KYCEALGLEK NWQMNTSCMV ECPVNCQLSD WSPWSECSQT CGLTGKMIRR RTVTQPFQGD   1320
GRPCPSLMDQ SKPCPVKPCY RWQYGQWSPC QVQEAQCGEG TRTRNISCVV SDGSADDFSK   1380
```

-continued

```
VVDEEFCADI ELIIDGNKNM VLEESCSQPC PGDCYLKDWS SWSLCQLTCV NGEDLGFGGI    1440
QVRSRPVIIQ ELENQHLCPE QMLETKSCYD GQCYEYKWMA SAWKGSSRTV WCQRSDGINV    1500
TGGCLVMSQP DADRSCNPPC SQPHSYCSET KTCHCEEGYT EVMSSNSTLE QCTLIPVVVL    1560
PTMEDKRGDV KTSRAVHPTQ PSSNPAGRGR TWFLQPFGPD GRLKTWVYGV AAGAFVLLIF    1620
IVSMIYLACK KPKKPQRRQN NRLKPLTLAY DGDADM                              1656
```

BIOMARKERS OF MEMBRANOUS GLOMERULONEPHRITIS

CROSS-REFERENCE TO RELATED APPLICATIONS

This application claims priority to European Application No. 21202650.4, filed on Oct. 14, 2021. The content of this application is hereby incorporated by reference in its entirety.

REFERENCE TO A SEQUENCE LISTING

The present application is accompanied by an ASCII text file as a computer readable form containing the sequence listing entitled, "004743US_SL.xml", created on Oct. 5, 2022, with a file size of 17,594 bytes, the content of which is hereby incorporated by reference in its entirety.

BACKGROUND OF THE INVENTION

Field of the Invention

The present invention relates to novel biomarkers of membranous glomerulonephritis (MGN), particularly biomarkers, such as autoantibodies and antigens present in subjects diagnosed with MGN. The invention provides in vitro methods and kits for diagnosis, prognosis and monitoring of MGN.

Description of the Related Art

Membranous glomerulonephritis (MGN) is an autoimmune kidney disease characterized by proteinuria, the presence of excess proteins in the urine, MGN develops when circulating antibodies bind antigens on the surface of the podocyte cells of the glomerular basement membrane of the kidney, which leads to activation of the complement system, disruption of the glomerular filtration barrier and development of proteinuria. For decades, the antigens that elicit the autoimmune reaction causing MGN remained unknown, and the molecular pathophysiology of the disease could not be characterized. Furthermore, it was impossible to make an antigen-specific diagnosis of MGN, Without an immunological biomarker serving as a marker for diagnostics and disease progression, the disease could only be diagnosed via biopsy. Therapeutic decisions were made based on the markers proteinuria and serum creatine, which are markers of kidney damage that occur once the disease has progressed and measurable damage has occurred. Thus, it was difficult to adapt possible therapies to disease progression, since early biomarkers and ways to characterize the disease were not available.

The first MGN target antigens, phospholipase A2 receptor 1 (PLA2R1) and thrombospondin type 1 domain-containing protein 7A (THSD7A) were discovered in 2009 and 2014, respectively. Together, they account for about 80% of patients with MGN. The discovery of these disease-causing antigens enabled the development of specific diagnostic markers, such as specific staining of renal biopsies for the respective antigens and detection of circulating antibodies in patient blood samples. In patients with PLA2R1 antibody-associated MGN, the level of circulating autoantibodies can not only predict the response to therapies, but also enable a prognosis with respect to renal insufficiency. Hence, the therapy for these patients can be adjusted based on their individual PLA2R1 antibody level and thus therapy can be adjusted with disease progression and pathogenesis.

Targeted therapies or biomarkers are not available for 20% of patients with MGN. Thus, there is a corresponding need for diagnosis, prognosis and targeted therapy for these patients. The development of further biomarkers aiding the therapy of MGN has been hindered by the molecular properties of the antigens. The epitopes recognized by autoantibodies in PLA2R1 and THSD7A are conformation dependent and cannot be detected by conventional methods, such as standard Western Blot methods.

The present inventors were able to develop a new biomarker for MGN that can be used to characterize MGN in patient blood samples in order to aid diagnosis, monitor disease progression and enable targeted therapy.

SUMMARY OF THE INVENTION

The problem underlying the present invention is solved by the subject matter of the attached independent and dependent claims.

It is an objective of the invention to provide effective methods for diagnosis and prognosis of membranous glomerulonephritis (MGN), particularly idiopathic membranous glomerulonephritis in a subject. Furthermore, it is an objective of the invention to provide non-invasive methods of determining therapeutic effectiveness and disease progression in subject with MGN. Preferably the MGN is an autoimmune MGN, more preferably associated with the presence of anti-NTNG1, such as anti-NTNG1 autoantibodies. Another objective is the provision and preparation of devices, assays and reagents for such an assay.

Surprisingly, the inventors were able to identify a novel autoantigen in membranous glomerulonephritis. Thus, the invention relates to the identification of Netrin G1 (NTNG1) as a novel autoantigen in membranous glomerulonephritis and providing methods of using NTNG1 and NTNG1 autoantibodies as a biomarker.

A first aspect of the invention relates to an in vitro method comprising detecting one or more autoantibodies recognizing, preferably binding specifically to, a Netrin G1 (NTNG1) polypeptide or one or more anti-NTNG1 antibody-binding fragments thereof in a biological sample obtained from a subject.

In one embodiment, the in vitro method further comprises the step of detecting any antigen-antibody complexes formed between the NTNG1 polypeptide or one or more anti-NTNG1 antibody-binding fragments thereof and anti-NTNG1 autoantibodies in the biological sample.

Hence, in one embodiment, the in vitro method of diagnosing membranous glomerulonephritis in a subject comprises the steps of (i) contacting a biological sample obtained from the subject with an NTNG1 polypeptide or one or more anti-NTNG1 antibody-binding fragments thereof, (ii) detecting any antigen-antibody complexes formed between the NTNG1 polypeptide or one or more anti-NTNG1 antibody-binding fragments thereof and anti-NTNG1 autoantibodies in the biological sample.

In one embodiment, detecting the antigen-antibody complexes comprises determining the presence of anti-NTNG1 autoantibodies.

In one embodiment, detecting the presence of any antigen-antibody complexes between the NTNG1 polypeptide or one or more anti-NTNG1 antibody-binding fragments thereof and anti-NTNG1 autoantibodies may result or results in a positive diagnosis for NTNG1-positive MGN or may aid in diagnosing NTNG1-positive MGN.

Without adequate biomarkers to measure the disease progression of MGN in a patient, it is not possible to determine therapeutic effectiveness or to adjust treatments or therapies to match the extend of disease progression. The inventors have surprisingly been able to show that NTNG1 serves as an autoantigen in MGN in a group of patients who do not produce autoantibodies to antigens commonly associated with MGN, and that levels of anti-NTNG1 autoantibodies in the blood of patients with MGN can be used to determine the effectiveness of treatment of the patient.

Hence, the invention also relates to an in vitro method of determining the effectiveness of a treatment for MGN in a subject, comprising (i) determining the level of anti-NTNG1 autoantibodies in a first biological sample obtained from a subject at a first time-point and (ii) determining the level of anti-NTNG1 autoantibodies in a second biological sample obtained from a subject at a second time-point, wherein a decrease in the level of anti-NTNG1 antibodies in the second time point compared to the first time point indicates that the treatment is effective, and/or an increase in the level of anti-NTNG1 autoantibodies in the second time point compared to the first time point indicates that the treatment is not effective.

In one embodiment, determining the level of anti-NTNG1 autoantibodies in a first or second sample comprises contacting a biological sample obtained from the subject with an NTNG1 polypeptide or one or more anti-NTNG1 antibody-binding fragments thereof and detecting any antigen-antibody complexes formed between the NTNG1 polypeptide or one or more anti-NTNG1 antibody-binding fragments thereof and anti-NTNG1 autoantibodies in the biological sample.

In one embodiment, the biological sample is a blood sample, such as whole blood, serum, capillary blood or plasma, preferably a serum sample. In another embodiment, the biological sample is a tissue sample, preferably kidney tissue.

Furthermore, the inventors found that levels of NTNG1 polypeptides or fragments thereof in the biological sample of a subject, containing at least one NTNG1 antigen that binds to anti-NTNG1 autoantibodies of subjects with MGN, can be used to make a prognosis and/or determine the therapeutic needs in said subjects.

Thus, a further aspect of the invention relates to an in vitro method for prognosis of MGN in a subject, comprising the steps of determining the expression level of NTNG1 polypeptide or one or more anti-NTNG1 antibody-binding fragments thereof in a biological sample obtained from said subject and comparing said expression level to a reference expression level, wherein an increased expression level of NTNG1 polypeptide or one or more anti-NTNG1 antibody-binding fragments thereof compared to said reference expression level is indicative of MGN or an increased likelihood of MGN, compared to an average subject, such as a healthy subject. Preferably, the biological sample is a tissue sample, more preferably a kidney biopsy.

In one embodiment, the reference level is determined by determining the expression level of NTNG1 polypeptide or one or more anti-NTNG1 antibody-binding fragments thereof in a group of subjects without NTNG1-associated MGN and calculating the mean level of NTNG1 polypeptide or one or more anti-NTNG1 antibody-binding fragments thereof in subjects without NTNG1-associated MGN.

In one embodiment, the expression level of NTNG1 polypeptide or one or more anti-NTNG1 antibody-binding fragments thereof in a biological sample is determined by contacting the biological sample with an anti-NTNG1 antibody or one or more NTNG1 antigen-binding fragments thereof.

In one embodiment, the anti-NTNG1 antibody comprises a full-length antibody or one or more antibody fragments capable of binding to one or more NTNG1 antigens.

In another embodiment, the expression level of NTNG1 polypeptide or one or more anti-NTNG1 antibody-binding fragments thereof is determined by detecting NTNG1 mRNA or fragments of NTNG1 mRNA, preferably wherein the fragments of NTNG1 mRNA are at least 12 nucleotides in length.

In a further aspect, the invention also provides a kit, optionally for detecting anti-NTNG1 or diagnosing and/or prognosing MGN in a subject, the kit comprising (i) an NTNG1 polypeptide or one or more anti-NTNG1 antibody-binding fragments thereof and/or (ii) a reagent for detection of an antigen-antibody complex formed between the NTNG1 polypeptide or one or more anti-NTNG1 antibody-binding fragments thereof and one or more anti-NTNG1 antibody present in the sample.

In one embodiment, the NTNG1 polypeptide or one or more anti-NTNG1 antibody-binding fragments thereof are capable of binding or binding specifically to anti-NTNG1 antibodies.

In one embodiment, the sample is a tissue sample, preferably a renal biopsy sample. Hence, in one embodiment, the biological sample is a blood sample or a renal biopsy sample. Preferably, the biological sample is a blood sample.

In one embodiment, the NTNG1 polypeptide or one or more anti-NTNG1 antibody-binding fragments thereof are soluble.

In one embodiment, the NTNG1 polypeptide or one or more anti-NTNG1 antibody-binding fragments thereof are isolated and/or recombinant.

In one embodiment, the NTNG1 polypeptide comprises an amino acid sequence with at least 70% identity to the amino acid sequence according to SEQ ID NO: 1. In another embodiment, the NTNG1 polypeptide comprises an amino acid sequence with at least 75%, at least 80%, at least 85%, at least 90%, at least 95%, at least 98%, at least 99%, or 100% identity to the amino acid sequence according to SEQ ID NO: 1.

Another aspect of the present invention relates to a method for isolating an antibody, preferably an autoantibody, binding to an NTNG1 polypeptide or one or more anti-NTNG1 antibody-binding fragments thereof, comprising the steps
 a) immobilizing on a device such as a carrier a polypeptide comprising an NTNG1 polypeptide or one or more anti-NTNG1 antibody-binding fragments thereof,
 b) contacting a sample such as a biological sample comprising an antibody with the polypeptide under conditions compatible with formation of a complex, wherein said antibody binds to said polypeptide,
 c) separating the complex formed in step a) from the sample, and
 d) separating the antibody from the polypeptide.

In one embodiment, the antibody, preferably autoantibody, is isolated from a biological sample such as a sample obtained from a subject or a patient having or suspected of having MGN.

Another aspect of the present invention relates to a method comprising the steps
 a) immobilizing a polypeptide comprising an NTNG1 polypeptide or one or more anti-NTNG1 antibody-binding fragments thereof on a device such as a carrier, b) contacting the device with a liquid, wherein a candidate drug is present and/or the liquid does not comprise a sample from a subject to be diagnosed, comprising an antibody binding specifically to a NTNG1 polypeptide or one or more anti-NTNG1 antibody-binding fragments thereof, c) contacting the carrier with a means for detecting an immobilized antibody, and d) detecting the presence, preferably in quantitative manner.

According to the present invention, an autoantibody binding specifically to a mammalian NTNG1 is provided, preferably in a solution comprising one or more, more preferably all from the group comprising an artificial buffer, a preservative and an artificial anticoagulant. In a preferred embodiment, the autoantibody is isolated. In one embodiment, the autoantibody is in a blood sample such as serum, wherein the blood sample is optionally diluted.

An artificial buffer is a buffer which is synthetic and/or may not occur in the body of the patient or at least at concentrations well below the concentration used. The buffer may be selected from the group comprising Tris, phosphate, Tricine, acetate, MOPS, MES, carbonate, citrate and HEPES.

In a preferred embodiment, the term "preservative" as used herein, refers to a substance inhibiting microbial growth and/or chemical degradation in a liquid solution and may preferably be selected from the group comprising azide, lactic acid, nitrate, nitrite, antibiotics, a protease inhibitor and ethanol.

In a preferred embodiment, the term "stabilizer", as used herein, is a reagent that stabilizes a proteinaceous molecule such as an antibody, for example by decreasing degradation, by decreasing unfolding or by decreasing loss of the molecule, for example as a result of non-specific absorption to a solid phase such as reaction vessel.

Examples of stabilizers include bovine serum albumin, casein and soybean protein. In a preferred embodiment, the autoantibody is in a blood sample from a subject, preferably human, suffering from MGN.

The autoantibody may be used as a positive control for detection assays, as a reagent for inhibiting renal function, for example in an experimental setup, as a labeled or non-labeled reagent for competitive assays or as a calibrator.

The invention further relates to a device such as a diagnostically useful carrier with a solid phase with an NTNG1 polypeptide or one or more anti-NTNG1 antibody-binding fragments thereof, immobilized on the solid phase, and a) a negative control and/or b) at least one additional diagnostically useful antigen, wherein the polypeptide or fragment thereof and the negative control or additional antigen are spatially separate on the carrier, or a first device such as a first diagnostically useful carrier with a solid phase comprising an NTNG1 polypeptide or one or more anti-NTNG1 antibody-binding fragments thereof, immobilized on the solid phase, and a second device such as a second diagnostically useful carrier comprising a solid phase comprising an immobilized a) negative control and/or b) at least one additional immobilized polypeptide comprising an antigen or a variant thereof.

In a preferred embodiment, the at least one additional antigen is at least one antigen, preferably all antigens from the group comprising PLA2R, THSD7A, NELL-1, Exostosin 1, Exostosin 2. Semaphorin3B, Protocadherin 7 and serine protease HTRA1.

The invention further relates to a use of a) the autoantibody according to the present invention or b) the combination of an NTNG1 polypeptide or one or more anti-NTNG1 antibody-binding fragments thereof and a means for detecting or capturing an autoantibody, preferably IgG antibody or c) the use of an NTNG1 polypeptide or one or more antibody-binding fragments thereof or d) the device according to the present invention for diagnosing MGN.

BRIEF DESCRIPTION OF THE DRAWINGS

FIG. 4A: Validation of NTNG1 as target antigen in the MGN index patient. Gentle Western Blot of different HGE protein samples (membrane fraction, cytoplasmic fraction and deglycosylated protein) probed with serum of the index patient. Ln, 1 HGE-membrane; Ln. 2 HGE cytoplasm; Ln. 3 HGE deglycosylated.

FIG. 4B: Validation of NTNG1 as target antigen in the MGN index patient. Gentle Western Blot of recombinantly expressed NTNG1 polypeptide probed with serum of the MGN index patient (Ln. 1), a healthy subject (Ln. 2), a PLA2R1-antibody positive patient (Ln. 3, MGN-patient), and a THSD7A-antibody positive patient (Ln. 4, MGN-patient).

DETAILED DESCRIPTION OF THE INVENTION

General Definitions

Figure 1:
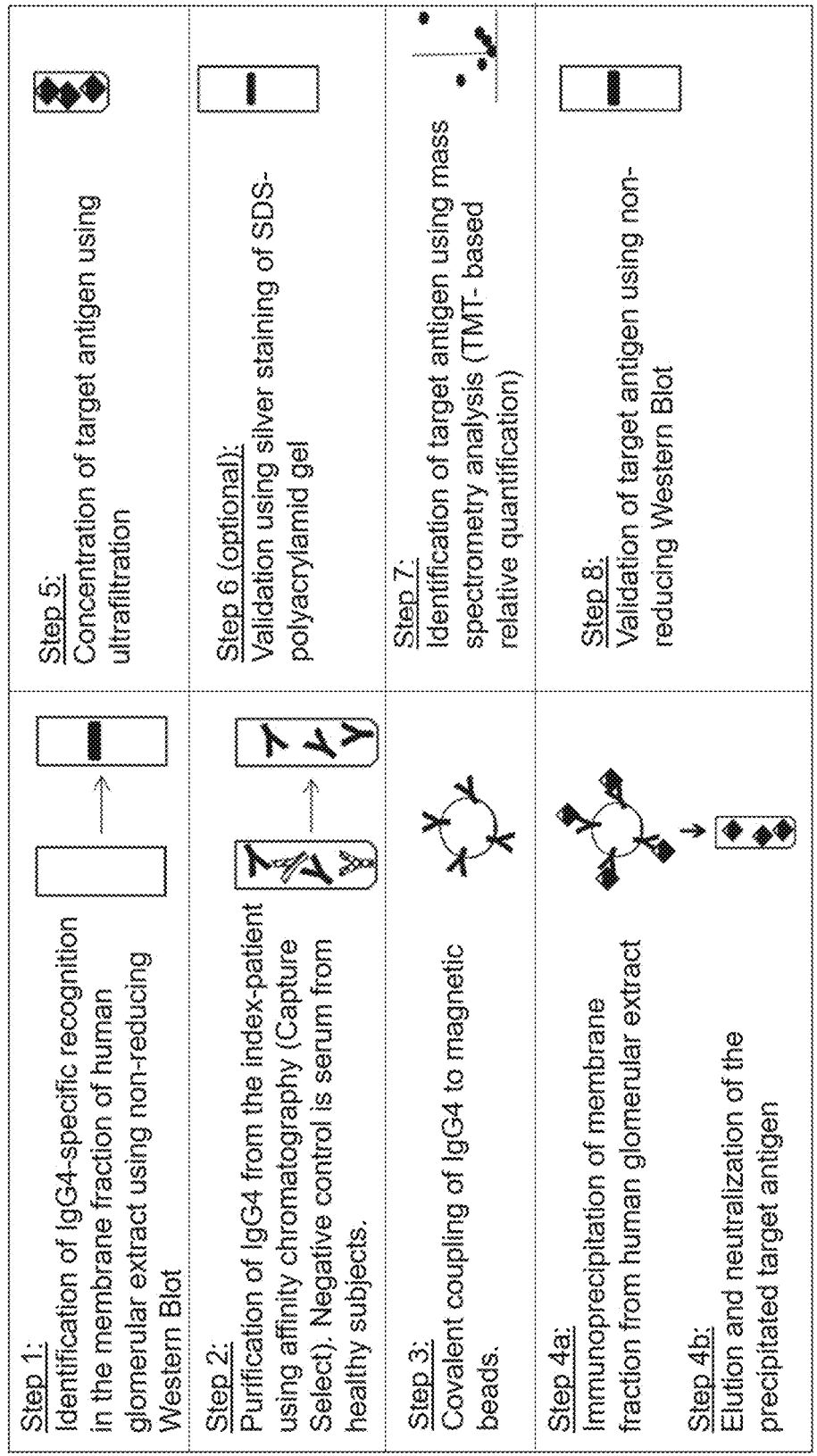
FIG. 1: Overview of method used to identify a novel target antigen in an index patient, including isolating IgG4-antibodies from the blood of the index patient, coupling of the purified IgG4 to magnetic beats, immunoprecipitation of bound antigen targets, concentration of elution fractions and identification of target antigen using mass spectrometry.

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto.

Where the term "comprising" is used in the present description and embodiments, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

The term "one or more", as used herein, comprises "at least one".

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

Technical terms are used by their common sense. If a specific meaning is conveyed to certain terms, definitions of terms will be given in the following in the context of which the terms are used.

The term "autoantibody" refers to an antibody that is produced by the immune system of a subject (or patient) and that is directed against a subject's (or patient's) own proteins, preferably autoantigens. Thus, an autoantibody is an endogenous molecule produced within a subject's body. Autoantibodies may attack the body's own cells, tissues, and/or organs, causing inflammation and cell injury. The subject is preferably a patient suspected of or actually suffering from a disease, preferably a mammalian, more preferably human patient. Such an autoantibody has a constant region, as have other antibodies of the same class from the same organism. Particularly preferably, the autoantibody is a mammalian autoantibody, even more preferably a human autoantibody, even more preferably a human autoantibody of class IgG, IgM or IgA, preferably IgG. The variable domain thereof is capable of binding specifically against the autoantigen. The constant domain binds specifically to molecules recognizing the constant domain of IgG class antibodies such as secondary antibodies. It has sequence elements shared by other IgG class antibodies from the same organism. The terms "autoantibody recognizing NTNG1" can be used interchangeably with "anti-NTNG1 autoantibody". The term "anti-NTNG1 antibody" also includes anti-NTNG1 autoantibodies.

The term "circulating autoantibody" refers to autoantibodies circulating within the body, for example within the blood circulatory system or the lymph system. Specifically, circulating autoantibodies are commonly detected in the serum of a subject.

The term "isolated" as used herein means that the molecule referred to as being isolated is free or essentially free of at least one component as it is found in nature. For example, the molecule, such as an autoantibody, may be free or essentially free from some or all components as it is found in its natural environment. Such components may comprise, for example in the case of an autoantibody, erythrocytes, leucocytes, thrombocytes, plasma, proteins, nucleic acids, salts, lipids, and nutrients.

The term "expression" or "gene expression" as used herein refers to the process of synthesis of a gene product, preferably a functional RNA or protein. Gene expression generally comprises DNA transcription, optionally RNA processing and in the case of protein-expressing genes, RNA translation.

The term "heterologous" (or exogenous or foreign or recombinant or non-native) polypeptide is defined herein as a polypeptide that is not native to the host cell, a polypeptide native to the host cell in which structural modifications, e.g., deletions, substitutions, and/or insertions, have been made by recombinant DNA techniques to alter the native polypeptide, or a polypeptide native to the host cell whose expression is quantitatively altered or whose expression is directed from a genomic location different from the native host cell as a result of manipulation of the DNA of the host cell by recombinant DNA techniques, or whose expression is quantitatively altered as a result of manipulation of the regulatory elements of the polynucleotide by recombinant DNA techniques e.g., a stronger promoter; or a polynucleotide native to the host cell, but integrated not within its natural genetic environment as a result of genetic manipulation by recombinant DNA techniques.

The terms "nucleic acid" or "nucleic acid molecule" or "nucleic acid sequence" or "nucleotide sequence" are used interchangeably herein to refer to a biomolecule composed of nucleotides. The nucleic acid molecule can be comprised within an eukaryotic or prokaryotic organism, a eukaryotic or prokaryotic cell, a cell nucleus or a cell organelle, as part of a genome or as an individual molecule; or it can be comprised within a plasmid, a vector, an artificial chromosome; a nucleic acid can also exist outside of a cell, in vesicles, viruses or freely circulating, it can be isolated in a suitable composition, in a fixed or frozen tissue or cell culture, or dried. The nucleic acid can be synthesized or naturally occurring, i.e. isolated from nature.

The terms "sequence identity", "% sequence identity", "% identity", "% identical" or "sequence alignment" are used interchangeably herein and refer to the comparison of a first nucleic acid sequence to a second nucleic acid sequence, or a comparison of a first amino acid sequence to a second amino acid sequence and is calculated as a percentage based on the comparison. The result of this calculation can be described as "percent identical" or "percent ID." A sequence identity may be determined by a program, which produces an alignment, and calculates identity counting both mismatches at a single position and gaps at a single position as non-identical positions in final sequence identity calculation. The sequence identity is determined over the entire length of the first and second nucleic acid sequence.

The terms "encoded protein" or "encoded amino acid" refers to a protein that consists of a chain of amino acids, which results from a sequence that is encoded by a nucleic acid molecule comprising three-nucleotide codons.

The terms "polypeptide", "protein" or "peptide" are used interchangeably herein and refer to amino acid sequences of a variety of lengths. The term polypeptide may also refer to the primary, secondary, tertiary, quaternary or quinary structure or a protein. Polypeptides can be in uncharged forms or as salts, either unmodified or modified by glycosylation, side chain oxidation, phosphorylation, citrullination or transglutamination. In certain embodiments, the polypeptide is a full-length native protein. In other embodiments, the polypeptide is a smaller fragment of the full-length protein. In still other embodiments, the amino acid sequence is modified by additional substituents attached to the amino acid side chains, such as N- or C-terminal added protein tags such as affinity tags, linkers, which may comprise 2-40, preferably to 30 amino acids with epitopes other than those from NTNG1 or not epitopes, glycosyl units, lipids, or inorganic ions such as phosphates, as well as modifications relating to chemical conversion of the chains such as oxidation of sulfhydryl groups. Thus, the term "polypeptide" is intended to include the amino acid sequence of the full-length native protein, or a fragment thereof, subject to those modifications that do not significantly change its specific properties.

Thus, in a preferred embodiment, the polypeptide may comprise chemical modifications, for example isotopic labels or covalent modifications such as glycosylation, phosphorylation, acetylation, decarboxylation, citrullination, methylation, hydroxylation and the like. The person skilled in the art is familiar with methods to modify polypeptides. Any modification is designed such that it does not abolish the biological activity of the polypeptide. Hence, the polypeptide has or retains biological activity. In a preferred embodiment, such biological activity is the ability to bind specifically to an autoantibody recognizing, preferably binding specifically to, NTNG1, as found in a patient suffering from MGN. For example, whether or not a NTNG1 polypeptide has such biological activity may be checked by determining whether or not the polypeptide of interest binds to an autoantibody from a sample of a patient which autoantibody recognizes, preferably binds to, wild type and/or full-length NTNG1, preferably as determined by ELISA using a commercial assay. In a preferred embodiment, the polypeptide may be flanked C-terminally or N-terminally by amino acids or amino acid sequences derived from NTNG1 or from any other proteins which do not prevent sterical access to the NTNG1 binding epitope comprised by the polypeptide, for example linkers and/or folded domains.

Polypeptides comprising any modification as described herein may be generated by fusion with other known polypeptides or variants thereof for example artificial linkers, affinity tags, other antigens and the like. Variants may comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In particular, the term "polypeptide" encompasses protein isoforms, i.e., variants that are encoded by the same gene, but that differ in their amino acid sequence or in other properties.

The term "antibody-binding fragment of an NTNG1 polypeptide" or "anti-NTNG1 antibody-binding fragment" relates to a molecule comprising an amino acid sequence derived from a protein that is not full length and comprises an antigen sequence which enables antibody binding. When used herein in connection with an antigen (e.g. NTNG1), "anti-NTNG1 antibody-binding fragment" refers to a fragment of the antigen that retains the ability of the antigen to bind specifically an anti-NTNG1 antibody to form an antibody-antigen complex. Suitable anti-NTNG1 antibody-binding fragments of an antigen may be identified by one skilled in the art by simple trials to ascertain their ability to bind specific autoantibodies of MGN.

The term "antigen" relates to a molecule or a molecular structure that can be bound by an antigen-specific antibody or a binding fragment thereof. An antigen can be composed of one or more epitopes, which can be linear structure. An antigen can also be composed of amino acids that form structure-dependent epitopes.

The "epitope" refers to the distinct surface features of an antigen that can act as points of interaction for specific antibodies. Antigenic molecules can comprise one or more epitopes. The minimum size of a linear epitope is about 4 amino acids and comprises one or more antibody contact residues.

An "autoantigen" is an endogenous molecule, a polypeptide, protein or protein complex, or a DNA or RNA molecule that is recognized by the immune system of a subject suffering from a specific autoimmune disease.

The terms "membranous nephropathy", "membranous glomerulopathy" or "membranous glomerulonephritis" or "MGN" refer to a slowly progressive disease of the kidney which is a frequent cause of adult nephrotic syndrome. Primary or Idiopathic membranous glomerulonephritis as described herein is considered to be an autoimmune disease targeting the glomerulus. Secondary membranous glomerulonephritis includes nephropathies caused by secondary factors such as systemic lupus erythematosus, hepatitis B or syphilis.

The "UniProt numbers" or "UniProt" or "UniProt Accession numbers" provided herein refer to the unique identifiers given to individual genes and proteins by the UniProt Consortium, which are available from their database at www.uniprot.org and commonly used as references in the field. UniProtKB (UniProt Knowledgebase) is a freely accessible database of protein sequence and functional information. The UniProt database includes manually annotated and reviewed entries (provided by the Swiss-Prot database) and automatically annotated and not manually reviewed entries (provided by TrEMBL database), many of which are derived from genome sequencing projects. TrEMBL includes translated coding sequences from the EMBL-Bank/GenBank/DDBJ nucleotide sequence database, and others.

As used herein, the term "biomarker" or "marker" refers to a measurable indicator of the presence or severity of a disease state. A biomarker can for example be used for diagnosis, to measure the progress of disease, or to evaluate effective therapeutic regimes. According to the invention, NTNG1 protein or an NTNG1 polypeptide or any anti-NTNG1 antibody-binding fragment thereof; and anti-NTNG1 autoantibodies are biomarkers of MGN, particularly idiopathic MGN. The efficacy of a candidate drug to treat MGN may be tested or monitored. A decreasing level of anti-NTNG1, specifically of anti-NTNG1 autoantibody, indicates an increased likelihood that the drug is effective.

The term "Phospholipase A2 Receptor 1" (PLA2R1, UniProt: Q13018) refers a type-1 transmembrane protein, which in humans is encoded by the PLA2R1 gene and predominantly expressed in the podocytes of the renal corpuscle of the kidney. It is known as an antigen that is predominant in about 70% of patients with idiopathic MGN.

The term "Thrombospondin type 1 domain-containing protein 7A" (THSD7A, UniProt: Q9UPZ6) refers to a protein highly expressed on podocytes which in humans is encoded by the THSD7A gene. It is a known antigen in MGN and the second most common antigen in MGN after PLA2R1.

As used herein, the term "patient" or "subject" is used interchangeably and refers to a human subject or another mammal subject (e.g., primate, dog, cat, goat, horse, pig, mouse, rat, rabbit, and the liked), that can be afflicted with a membranous nephropathy, particularly an idiopathic MGN. Preferably, the patient or subject is a human patient or subject. A patient suspected to have MGN has typically been diagnosed based on a kidney biopsy or due to the presence of a biomarker associated with MGN.

The term "biological sample" is used herein in its broadest sense. A biological sample is generally obtained for a subject. Said subject is mammal, preferably human. Typically, biological sample is generally obtained from a patient or subject. Typically, said sample comprises a representative set of autoantibodies or autoantigen. Hence, said biological sample may be a blood sample or a tissue sample. The tissue sample is preferably a kidney biopsy sample.

A sample may be of any biological tissue or fluid with which biomarker(s) of the present invention may be assayed. Such samples include, but are not limited to, bodily fluids which may or may not contain cells, e.g., blood (e.g., whole blood, serum or plasma) or urine. Such samples also include biopsies (for example kidney biopsy). The term biological sample also encompasses any material derived by processing a biological sample. Derived materials include, but are not limited to, cells (or their progeny) isolated from the sample or proteins extracted from the sample. Processing of a biological sample may involve one or more of: filtration, distillation, extraction, concentration, inactivation of interfering components, addition of reagents, and the like.

In the context of the present invention, the term "control", when used to characterize a subject, refers to a subject that is healthy or to a patient that has been diagnosed with a specific disease other than renal disease. The term "control sample" refers to one, or more than one sample, that has been obtained from a healthy subject or from a patient diagnosed with a disease other than renal disorder. A control sample as used herein may also be a sample from a patient diagnosed with PLA2R1-positive or THSD7A-positive MGN.

As used herein, the term "level" refers to the quantity of a molecule in a biological sample. For example, "anti-NTNG1 autoantibody level" refers to the number of detectable anti-NTNG1 autoantibody in a sample. The number may be a total or absolute number, or the number may be relative to a control or reference measurement. The level may be determined numerically, or it may be determined by measuring a secondary signal, such as fluorescence intensity. The level may also be expressed binary by presence or absence of the measured molecule, i.e. the level may be positive or negative, Antibody "level" can also refer be called "titer". When referring to a polypeptide or protein, "level" may also refer to the expression level of the polypeptide or protein.

As used herein, the term "reference level" refers to a level measured in a biological sample obtained from a control or preferably to an average of several levels measured in biological samples obtained from several controls.

As used herein, the term "diagnosis", "diagnosing" or "diagnostic" is used on its broadest sense and encompasses diagnosis, prognosis, theragnosis and monitoring in membranous nephropathy and MGN. As used herein, the term "theragnosis" refers to the identification, for example by diagnostic methods, of patients who might benefit from a particular therapy and, optionally, the subsequent treatment of said patients.

Thus, the term "diagnosis" may refer to any kind of procedure aiming to obtain information instrumental in the assessment whether a patient, known or an anonymous subject from a cohort, suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient or patients in general with regard to a certain treatment, for example the administration of immunosuppressive drugs, or to find out whether a sample is from such a patient. Such information may be used for a clinical diagnosis but may also be obtained by an experimental and/or research laboratory for the purpose of general research, for example to determine the proportion of subjects suffering from the disease in a patient cohort or in a population. In other words, the term "diagnosis" comprises not only diagnosing, but also prognosticating and/or monitoring the course of a disease or disorder, including monitoring the response of one or more patients to the administration of a drug or candidate drug, for example to determine its efficacy. While the result may be assigned to a specific patient for clinical diagnostic applications and may be communicated to a medical doctor or institution treating said patient, this is not necessarily the case for other applications, for example in diagnostics for research purposes, where it may be sufficient to assign the results to a sample from an anonymized patient. Thus, in some embodiments, the person to be diagnosed, i.e., the "subject" or "patient", is an anonymous blood donor whose blood may be donated or used to obtain therapeutically or diagnostically useful antibodies. The term "diagnosis" also refers to negative diagnosis, i.e., the case where no autoantibodies recognizing, preferably specifically binding to, NTNG1 are found in a sample from a patient. In these embodiments, the absence of autoantibodies recognizing, preferably specifically binding to, NTNG1 indicates that the patient may suffer from a disease other than a disease associated with the presence of said autoantibodies, as described herein, Thus, in one embodiment, "diagnosis" also includes the case where the absence of an autoantibody recognizing, preferably specifically binding to, NTNG1 helps excluding certain diseases, such as the diseases associated with the presence of such antibody, as described herein, such as MGN, which may lead to the indirect diagnosis of another disease. Thus, "diagnosing" and similar terms also include "aiding in the diagnosis" of a certain disease such as MGN. In another preferred embodiment, the detection of an autoantibody recognizing, preferably specifically binding to, NTNG1 is considered to imply a definitive diagnosis of an autoimmune disease such as MGN because of the presence of the autoantibody.

The terms "NTNG1-negative patient", "PLA2R1-negative patient or "THSD7A-negative patient" (or subject) refers to a patient whose serum contains no autoantibodies or at least no detectable levels of autoantibodies directed against the respective antigen. The terms "NTNG1-positive patient", "PLA2R1-positive patient or "THSD7A-positive patient" refer to a patient whose serum contains autoantibodies directed against the respective protein.

As used herein; the term "contacting" or "reacting" means bringing two compounds or molecules close enough to each other that they can chemically, electrically or physically interact. This interaction may be due to forces between molecules and may involve bonding and unhanding of molecules. Contacting may take place in solution or between solutions, on a solid support, between a liquid and solid phase; between a liquid and gaseous phase, between a solid and gaseous phase, within one or more gaseous phases or within a cell or organism or between cells and organism.

Novel Biomarker Netrin G1

Netrin G1 (NTNG1, UniProt: Q9Y212), which is in humans encoded by the gene NTNG1, is a secreted glycoprotein of about 50 kDa size. It binds to the cell membrane on the extracellular side with a glycosylphosphatidylinositol (GPI) anchor. Thus, NTNG1 is exposed on the cell surface of podocytes and is able to bind circulating antibodies. Podocytes are specialized epithelial cells that cover the outer surfaces of glomerular capillaries.

Several isoforms of NTNG1 exist, of which isoform 3 represents the full-length protein. Table 1 provides information about the different isoforms and changed or missing amino acid features compared in relation to isoform 3.

TABLE 1

Overview of NTNG1 isoforms

| Isoform | Region | MW (not processed) |
|---|---|---|
| 3 (also 1A) | M1-F539 | 60541 |
| 2 (also 1F) | M1-C364<br>363-364 NC → SK | 41759 |
| 1 (also 1C) | 363-463 missing<br>464-464 P → T | 49340 |
| 4 (also 1D) | 364-464<br>CECFGHSNRC . . . GNSWHYGCQP →<br>PPKFNRIWPN . . . SVQVANHKRA | 53946 |
| 5 (also 1E) | 364-385<br>CECFGHSNRCSYIDLLNTVICV →<br>PPKFNRIWPNISSLEVSNPKQA<br>386-464 missing | 51858 |
| 6 (also 1G) | 419-463: missing<br>464-464 P → A | 55660 |

As a secreted protein, NTNG1 comprises domains that are removed upon maturation and processing (Table 2). The unprocessed NTNG1 polypeptide has an amino acid sequence according to SEQ ID NO: 1. The propeptide, comprising amino acids 511-539 is removed from the mature from. Hence, the mature NTNG1 polypeptide sequence is an amino acid sequence according to SEQ ID NO: 2. Furthermore, NTNG1 polypeptide comprises a signal peptide which comprises amino acids 1-28. Signal peptides are commonly cleaved off from presecretory polypeptides by signal peptidase during or immediately after insertion into the membrane. Hence, the fully processed NTNG1 polypeptide, once secreted, has an amino acid sequence according to SEQ ID NO: 3.

TABLE 2

Overview of NTNG1 domains

| Domain | amino acid |
|---|---|
| signal peptide | 1-28 |
| Laminin N-terminal domain | 46-296 |
| Laminin EGF-like domain 1 | 297-356 |
| 2 | 364-419 |
| 3 | 420-469 |
| GPI anchor | 510 (amidated serine) |
| Removed from mature form | 511-539 |

In one embodiment, the NTNG1 polypeptide comprises an amino acid sequence with at least 70% identity to the amino acid sequence according to SEQ ID NO: 3. In another embodiment, the NTNG1 polypeptide comprises an amino acid sequence with at least 75%, at least 80%, at least 85%, at least 90%, at least 95%, at least 98%, at least 99%, or 100% identity to the amino acid sequence according to SEQ ID NO: 3.

In another embodiment, the NTNG1 polypeptide comprises an amino acid sequence with at least 70% identity to the amino acid sequence according to SEQ ID NO: 1. In another embodiment, the NTNG1 polypeptide or one or more anti-NTNG1 antibody-binding fragments thereof comprise an amino acid sequence with at least 75%, at least 80%, at least 85%, at least 90%, at least 95%, at least 98%, at least 99%, or 100% identity to the amino acid sequence according to SEQ ID NO: 1.

In another embodiment, the NTNG1 polypeptide comprises an amino acid sequence with at least 70% identity to an amino acid sequence selected from the group consisting of SEQ ID NO: 5, SEQ ID NO: 6, SEQ ID NO: 7 or SEQ ID NO: 8. In another embodiment, the NTNG1 polypeptide comprises an amino acid sequence with at least 80% identity to the amino acid sequence selected from the group consisting of SEQ ID NO: 5, SEQ ID NO: 6, SEQ ID NO: 7 or SEQ ID NO: 8. In another embodiment, the NTNG1 polypeptide comprises an amino acid sequence with at least 90% identity to the amino acid sequence selected from the group consisting of SEQ ID NO: 5, SEQ ID NO: 6, SEQ ID NO: 7 or SEQ ID NO: 8. In another embodiment, the NTNG1 polypeptide comprises an amino acid sequence according to an amino acid sequence selected from the group consisting of SEQ ID NO: 5. SEQ ID NO: 6, SEQ ID NO: 7 or SEQ ID NO: 8.

As used herein, the expression "anti-NTNG1 antibody-binding fragment of the NTNG1 polypeptide" or "fragment of NTNG1" refers to a continuous amino acid sequence comprised in the full-length NTNG1 polypeptide that comprises an antigen sequence that can recognize and bind an anti-NTNG1 antibody, and is able to participate in the formation of an antigen-antibody complex with one or more anti-NTNG1 antibodies.

In one embodiment, said anti-NTNG1 antibody-binding fragment of the NTNG1 polypeptide comprises at least 10 consecutive amino acids of the entire amino acid sequence of NTNG1. In another embodiment, said anti-NTNG1 antibody-binding fragment of NTNG1 comprises at least 20, at least 40, at least 60, at least 80, at least 100, at least 120, at least 140, at least 160, at least 180, at least 200, at least 250, at least 300, at least 350, at least 400, at least 450, at least 500 or 539 consecutive amino acids of the entire amino acid sequence of full-length NTNG1 (SEQ ID NO: 1).

In another embodiment, the anti-NTNG1 antibody-binding fragment of NTNG1 comprises at least 5%, at least 10%, at least 20%, at least 30%, at least 40%, at least 50%, at least 60%, at least 70%, at least 75%, at least 80%, at least 85%, at least 90%, at least 95%, at least 98%, at least 99% or 100% of the amino acid sequence of full-length NTNG1, i.e. SEQ ID NO: 1. In another embodiment, the anti-NTNG1 antibody-binding fragment of NTNG1 comprises at least 10%, at least 20%, at least 30%, at least 40%, at least 50%, at least 60%, at least 70%, at least 75%, at least 80%, at least 85%, at least 90%, at least 95%, at least 98%, at least 99% or 100% of the amino acid sequence of mature NTNG1, i.e. SEQ ID NO: 3.

Preferably, the anti-NTNG1 antibody-binding fragment of NTNG1 is recognized by an autoantibody directed against NTNG1. Determining the ability of the fragment to interact with said autoantibodies and detecting antibody-antigen complexes between the NTNG1 polypeptide or one or more anti-NTNG1 antibody-binding fragments thereof and anti-NTNG1 autoantibodies can be accomplished by one of the methods described herein or by methods known in the art for determining direct binding. Such methods include co-immunoprecipitation, pull down assay, crosslinking assays, gel electrophoresis and immunoblots (Western Blot, Dotplot), ELISA (enzyme-linked immunosorbent assay), EIA (enzyme immunoassay), FRET (fluorescence resonance energy transfer), luciferase assay, immunohistochemistry, flow cytometry, co-crystallization, or mass spectrometry.

In a preferred embodiment, anti-NTNG1 antibody or a complex comprising NTNG1, such as a complex comprising NTNG1 polypeptide or one or more anti-NTNG1 antibody-binding fragments thereof or any other analyte, such as an analyte recognizing NTNG1 antibody, is detected using a detection method selected from the group comprising immunodiffusion, immunoelectrophoresis, light scattering immunoassays, agglutination, labeled immunoassays such as those from the group comprising radiolabeled immunoassay, enzyme immunoassays, more preferably ELISA, chemiluminescence immunoassays, preferably electrochemiluminescence immunoassay, and immunofluorescence, preferably indirect immunofluorescence. A competitive assay, a capture bridge assay, an immunometric assay, a class-specific second antibody on the solid phase, a direct or indirect class capture assay may also be used. The principle of each of these formats is detailed in The Immunoassay Handbook, 3rd edition, edited by David Wild, Elsevier, 2005. The detection of the anti-NTNG1 is preferably carried out under non-reducing conditions.

Methods of the Invention

Anti-NTNG1 Autoantibodies in Subjects with MGN

A first aspect of the invention relates to an in vitro method, optionally an in vitro method of diagnosing membranous glomerulonephritis (MGN) in a subject, comprising detecting one or more autoantibodies recognizing a Netrin G1 (NTNG1) polypeptide or one or more anti-NTNG1 antibody-binding fragments thereof in a biological sample obtained from a subject.

In one embodiment, the in vitro method further comprises the step of (i) contacting a biological sample obtained from the subject with an NTNG1 polypeptide or one or more anti-NTNG1 antibody-binding fragments thereof, and (ii) detecting any antigen-antibody complexes formed between the NTNG1 polypeptide or one or more anti-NTNG1 antibody-binding fragments thereof and anti-NTNG1 autoantibodies in the biological sample.

In one embodiment, detecting the antigen-antibody complexes between the NTNG1 polypeptide or one or more anti-NTNG1 antibody-binding fragments thereof and anti-NTNG1 autoantibodies comprises determining the presence of anti-NTNG1 autoantibodies.

In one embodiment, detection of antigen-antibody complexes between the NTNG1 polypeptide or one or more anti-NTNG1 antibody-binding fragments thereof and anti-NTNG1 autoantibodies formed in the biological sample may lead to a positive diagnosis of the subject. In many cases the mere detection of the anti-NTNG1 autoantibody, in other words determining whether or not detectable levels of the antibody are present in the sample, is sufficient for the diagnosis. In a more preferred embodiment, this may involve determining whether the concentration is at least 10%, preferably 20%, 50%, 100%, 200%, 500%, 1.000%, 2.000%, 2.500%, 5.000%, 1.0000%, 2.0000%, 5.0000%, 100.000%, 1.000.000% or 10.000.000% times higher than the concentration of the antibody of interest found in the average healthy subject. If the autoantibody can be detected, this will be information instrumental for the clinician's diagnosis. It may indicate an increased likelihood that the patient suffers, suffered or will suffer from MGN.

The person skilled in the art will appreciate that a clinician does usually not arrive at the conclusion whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other non-invasive methods such as polysomnography, to arrive at a conclusive diagnosis. See Baenkler H. W, (2012), General aspects of autoimmune diagnostics, in Renz, H., Autoimmune diagnostics, 2012, de Gruyter, page 3. The value of a diagnostic agent or method may also reside in the possibility to rule out one disease, thus allowing for the indirect diagnosis of another. In a preferred embodiment, the meaning of any symptoms or diseases referred to throughout this application is in line with the person skilled in the art's understanding as of the filing date or, preferably, earliest priority date of this application as evidenced by textbooks and scientific publications. In a preferred embodiment, the inventive methods or uses or products are not used, taken alone, to arrive at a definite, final diagnosis.

The inventive teachings may also be used in a method for preventing or treating a disease, preferably after a diagnosis according to the present invention, comprising the steps a) reducing the concentration of autoantibodies binding to the inventive polypeptide in the subject's blood and/or b) administering one or more immunosuppressive pharmaceutical substances, preferably selected from the group comprising rituximab, prednisone, methylprednisolone, cyclophosphamide, mycophenolate mofetil, intravenous immunoglobulin, tacrolimus, cyclosporine, methotrexate and azathioprine.

According to the present invention, a kit is provided, comprising a cell expressing, preferably overexpressing the NTNG1 polypeptide or one or more anti-NTNG1 antibody-binding fragments thereof, or the device, e.g. carrier, or the NTNG1 polypeptide or one or more anti-NTNG1 antibody-binding fragments thereof and further comprising one or more, preferably all reagents from the group comprising a secondary antibody, preferably labeled with a detectable label, a washing solution, a positive control, a negative control, a detergent, a cover glass, a mounting medium and a physiological salt solution, preferably PBS, or salt required to prepare it.

In a preferred embodiment, the positive control is a diluted sample, preferably blood from a patient suffering from MGN and comprising anti-NTNG1 or a monoclonal antibody binding specifically to NTNG1 polypeptide, preferably recognized by human IgG antibodies. The negative control may be a diluted sample from a healthy subject, for example a blood donor. The kit may comprise instructions how to carry out the assay. The kit may comprise a calibrator, preferably a set of at least three calibrators. In a preferred embodiment, the term "calibrator", as used herein, refers to a reagent that may be used to calibrate an assay, in particular set up a reference range or a calibration curve. In a preferred embodiment, the calibrator is an antibody which binds to the NTNG1 and/or the polypeptide comprising NTNG1 coated on a device and is recognized by a secondary antibody recognizing the antibody to be detected, more preferably IgG, most preferably human IgG. A set of calibrators may comprise at least 3, 4 or 5 solutions each comprising different known concentrations of the calibrator. The concentrations between the calibrator with the lowest concentration and the calibrator with the highest concentration may be at least 1:10, 1:20, 1:50, 1:100, 1:200, 1:500 or 1:1000. Preferably, the secondary antibody is a secondary antibody binding specifically to IgG class antibodies, preferably human IgG class antibodies. In a preferred embodiment, the kit comprises the NTNG1 polypeptide or one or more anti-NTNG1 antibody-binding fragments thereof, optionally comprising a detectable label. The kit may be used for detecting a mammalian antibody to NTNG1 in a sample, preferably a human antibody to NTNG1 in a sample, more preferably a blood sample. The kit may be used for diagnosing, aiding in the diagnosis of NTNG1 or for identifying a subject having an increased risk of suffering from NTNG1 in the past, present or future.

Another aspect of the invention relates to a method comprising the step of detecting the presence or absence of anti-NTNG1 antibody, in a sample.

In a preferred embodiment, the method, autoantibody, device or polypeptide or fragment thereof of the present invention may be for diagnosing or aiding in the diagnosis of a nephrological autoimmune disease, preferably MGN, or identifying a subject having an increased risk of suffering from the disease in the past, presence or future. In another preferred embodiment, the method, autoantibody, device or polypeptide or fragment thereof of the present invention may be for distinguishing an autoimmune nephrological disease from another nephrological disease not associated with the presence of anti-NTNG1.

In a preferred embodiment, any information, result or data obtained according to the present invention, for example demonstrating the presence of absence of anti-NTNG1 in a sample or the expression of NTNG1, may be communicated to the patient or a medical doctor treating the patient orally, preferably by telephone, in a written form, preferably fax or letter, or in an electronic form via fax or via the internet, for example as an email or text message.

In one embodiment, the NTNG1 polypeptide or one or more anti-NTNG1 antibody-binding fragments thereof is from human NTNG1. In another embodiment, the NTNG1 polypeptide or one or more anti-NTNG1 antibody-binding fragments thereof is from a different mammalian species, such as non-human primate, pig, sheep, horse, donkey, rabbit, rat or mouse.

In one embodiment, the NTNG1 polypeptide may be a full-length NTNG1 polypeptide according to SEQ ID NO: 1. In another embodiment, the NTNG1 polypeptide may be a mature, processed NTNG1 polypeptide according to SEQ ID NO: 3.

In one embodiment the NTNG1 polypeptide or one or more anti-NTNG1 antibody-binding fragments thereof is an isolated and/or a recombinant polypeptide.

The NTNG1 polypeptide or one or more anti-NTNG1 antibody-binding fragments thereof may be recombinantly expressed in a cell or organism. Hence, in one embodiment, the NTNG1 polypeptide or one or more anti-NTNG1 antibody-binding fragments thereof is a recombinant polypeptide or one or more antibody-binding fragments thereof. In another embodiment, the recombinant polypeptide or one or more antibody-binding fragments is produced in recombinant mammalian cells.

In a preferred embodiment, the antibody, preferably anti-NTNG1, such as anti-NTNG antibody, or the complex to be detected, binds specifically to its interaction partner, preferably NTNG1 polypeptide. In a preferred embodiment, the term "binding specifically", as used herein, preferably means that the binding reaction is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7.

In another preferred embodiment, the methods and products according to the present invention may be used for determining the concentration of an antibody binding specifically to NTNG1 in a liquid, which may not be a sample from a subject or only a processed sample, for example for preparing a calibrator or set of calibrators with known relative or absolute concentrations or standardizing solutions.

Methods for expressing polypeptides in cells or organisms are known in the art and include cell/tissue culture, batch cell culture, fed-batch culture or suspension culture or in vitro cell free expression systems. Cells or organisms capable of producing the NTNG1 polypeptide or one or more antibody-binding fragments include mammalian cells, insect cells, yeasts, fungal cells, bacterial cells, plant and algal cells. Preferably, the NTNG1 polypeptide or one or more antibody-binding fragments are produced in mammalian cells. Suitable mammalian cell lines include human embryonic kidney (HEK) 293, human fibrosarcoma HT-1080, human embryonic retinal PER.C6, HeLa, Chinese hamster ovary (CHO), hamster kidney BHK 21, mouse myeloma NS0, and murine 0127.

Mammalian expression systems can be transiently induced to produce the polypeptide of the invention by transfection, transduction or infection or a suitable vector. The mammalian cell may also be a stable cell lines in which the expression construct is stably integrated into the host genome at one or more locations.

Suitable non-mammalian cells are insect cells optimized for protein expression such as *Drosophila melanogaster* S2 cells, *Spodoptera frugiperda* Sf9 or Sf21 cells or *Trichoplusia ni* BTI-TN-5B1-4 (High Five) cells.

Transient expression is the temporary expression of genes that are expressed for a short time after a nucleic acid has been introduced into the cell or organism. Transient expression may be achieved by transfection with a plasmid vector or viral transduction.

Stable integration may be achieved using methods known in the art, including virus transduction, plasmid, BAC (bacterial artificial chromosome) or YAC (yeast artificial chromosome) transfection, transposon-mediated transfer and integration, site-specific integration and gene editing methods such as zinc finger nucleases, CRISPR/Cas9 or TALENs.

Methods of isolating or purifying NTNG1 polypeptide or one or more anti-NTNG1 antibody-binding fragments thereof from the cell or organism or culture medium are described herein and known in the art and include spin columns and kits, liquid chromatography; such as FPLC or HPLC, magnetic beads, filter plates, or resins.

In one embodiment, the NTNG1 polypeptide or one or more anti-NTNG1 antibody-binding fragments thereof may comprise an epitope or purification tag, preferably selected from His-tag, GS-tag, FLAG-tag, c-Myc tag or HA-tag. In a preferred embodiment, the NTNG1 polypeptide or one or more anti-NTNG1 antibody-binding fragments thereof may comprise a tag, such as an affinity tag, wherein the tag preferably is selected from the group comprising His tag, GST tag, E tag, FLAG tag, HA tag, myc tag. V5 tag; S tag, SnoopTag, SpyTag, SofTag, Strep tag, Strep tag II, T7 Epitope tag, biotin tag, ALFA-tag, AviTag, C-Tag, calmodulin tag, iCap tag, polyglutamate tag, polyarginine tag, NE-tag, Rho1D4-tag, SBP-tag, Softag 1, Softag 3, Spot-tag, T7-tag, TC tag, Ty tag, VSV-tag, and Xpress tag. The tag may also be a fluorescent tag, such as a fluorescent protein or FRET label, or a radiolabel. In another embodiment, the NTNG1 polypeptide or one or more anti-NTNG1 antibody-binding fragments thereof may be untagged.

In one embodiment, the invention also provides a vector for the expression of an NTNG1 polypeptide or one or more anti-NTNG1 antibody-binding fragments thereof, preferably wherein the vector comprises an expression cassette comprising a promoter and a nucleic acid molecule encoding the NTNG1 polypeptide or one or more anti-NTNG1 antibody-binding fragments thereof of the invention. In one embodiment, the vector may comprise a nucleic acid molecule with at least 70%, at least 75%, at least 80%, at least 85%, at least 90%, at least 95%, at least 98%, at least 99% or 100% identity with the nucleic acid according to SEQ ID NO: 4.

In one embodiment, the vector is a eukaryotic expression vector or a viral vector. The promoter may be any suitable promoter for expression in the chosen system, for example CMV, T7, lac operator, EF1alpha, Tet operator, EpIE2, SV40, MT, UbC, RSV, AUG1, CMV/EF1alpha, FLD1, TK, Gal4 UAS/E1 b, trc, AOX1, Polyedrin or copia.

In certain embodiments, the NTNG1 polypeptide or one or more anti-NTNG1 antibody-binding fragments thereof is immobilized onto a solid carrier or support (e.g., a bead, microplate or array). Hence some aspects of the invention refer to a diagnostic device on which the NTNG1 polypeptide or one or more anti-NTNG1 antibody-binding fragments thereof is immobilized. Accordingly, in some embodiments, the method of the invention involves the use of a diagnostic device comprising, preferably coated with, the NTNG1 polypeptide or one or more anti-NTNG1 antibody-binding fragments thereof. In a preferred embodiment, the device is selected from the group comprising a glass slide, preferably for microscopy, a biochip, a microtiter plate, a lateral flow device, a test strip, a membrane, preferably a line blot, a chromatography column and a bead, preferably a magnetic or fluorescent bead. In another preferred embodiment, the term "coated with" means that a polypeptide such as the NTNG1 polypeptide or an antibody or another agent is immobilized on a solid surface of a device or the polypeptide and the device are configured for such an immobilization. A particularly preferred way for the configuration or the immobilization is using a carrier and/or means modified such that one of the agent or polypeptide to be immobilized comprises an affinity tag such as biotin and the other comprises a ligand to the affinity tag such as streptavidin. Affinity tags that can be used are known to the skilled person and include, without limitation, the group of tags comprising His, immobilized nickel, glutathione, chitin, 18A, ACP, Aldehyde, Avi, BCCP, Calmodulin, Chitin binding protein, E-Tag, ELK16, FLAG, flash, poly glutamate, poly aspartate, GST, GFP, HA, Isope, maltose binding protein, myc, nus, NE, ProtA, ProtC, Tho1d4, S-Tag, SnoopTag, SpyTag, SofTag, Streptavidin, Strep-tag II, T7 Epitope Tag, TAP, TO, Thioredoxin, Ty, V5, VSV, biotin. Xpress Tag and a recombinant antibody binding to the ligand to an affinity tag. In a preferred embodiment, a ligand to an affinity tag, as used herein, is an artificial entity binding specifically to an affinity tag, typically a chemically synthesized modification or a recombinant protein or peptide attached to a molecule of interest. The ligand to an affinity tag depends on the type of affinity tag chosen. Such ligands are known in the art. Alternatively, one of the carrier or the polypeptide or agent to be immobilized may comprise reactive chemical groups such as thiol, amino, epoxide, ester and anhydride groups which form covalent or non-covalent bonds with reactive chemical groups associated with the other. The device may comprise a negative control, for example a polypeptide which does not bind specifically to anti-NTNG1, preferably from human, preferably spatially separate from the NTNG1 polypeptide or one or more anti-NTNG1 antibody-binding fragments.

The diagnostic methods of the present invention involve detection of an antigen-antibody complex formed between the biomarker of the invention (e.g. NTNG1 polypeptide or one or more anti-NTNG1 antibody-binding fragments thereof) and an autoantibody present in the biological sample tested. This detection is indicative of the presence of autoantibodies (namely anti-NTNG1 autoantibodies or antigen-binding fragments thereof) in said sample.

The detection of an antibody-antigen complex between the NTNG1 polypeptide or one or more anti-NTNG1 antibody-binding fragments thereof and anti-NTNG1 autoantibodies may be performed by any suitable method. For example, the antibody-antigen complex between the NTNG1 polypeptide or one or more anti-NTNG1 antibody-binding fragments thereof and anti-NTNG1 autoantibodies may be detected using an immunoassay. Examples of immunoassays include radioimmunoassay, enzyme immunoassays (EIA), enzyme-linked immunosorbent assays (ELISA), immunofluorescence or immunoprecipitation. To this end, the NTNG1 polypeptide or one or more anti-NTNG1 antibody-binding fragments thereof is immobilized on a solid surface and the biological sample is brought into contact with the bound polypeptide or fragments thereof under conditions allowing formation of an antigen-antibody complex between the NTNG1 polypeptide or one or more anti-NTNG1 antibody-binding fragments thereof and anti-NTNG1 autoantibodies. Following incubation, the antigen-antibody complex between the NTNG1 polypeptide or one or more anti-NTNG1 antibody-binding fragments thereof and anti-NTNG1 autoantibodies can then be detected using any secondary IgG antibody labelled, for example human IgG antibody for samples from human subjects, with a detectable moiety.

The antibody-antigen complex between the NTNG1 polypeptide or one or more anti-NTNG1 antibody-binding fragments thereof and anti-NTNG1 autoantibodies may also be detected using an immunoblot, such as the Western Blot described herein. In this case, the NTNG1 polypeptide or one or more anti-NTNG1 antibody-binding fragments thereof are immobilized in a carrier such as a polyacrylamide gel. Then, the NTNG1 polypeptide or one or more anti-NTNG1 antibody-binding fragments thereof are transferred to a blotting membrane. The biological sample is added and the antigen-antibody complex between the NTNG1 polypeptide or one or more anti-NTNG1 antibody-binding fragments thereof and anti-NTNG1 autoantibodies forms on the membrane. The antigen-antibody complex between the NTNG1 polypeptide or one or more anti-NTNG1 antibody-binding fragments thereof and anti-NTNG1 autoantibodies can then be detected using any secondary IgG antibody labelled, for example human IgG antibody for samples from human subjects, with a detectable moiety.

Preferably, the formation of antigen-antibody complex between the NTNG1 polypeptide or one or more anti-NTNG1 antibody-binding fragments thereof and anti-NTNG1 autoantibodies is achieved under non-reducing conditions.

The secondary antibody may be labeled with any detectable moiety, i.e., any entity that, by its chemical nature, provides an analytically identifiable signal allowing detection of the ternary complex between the NTNG1 polypeptide or one or more anti-NTNG1 antibody-binding fragments thereof and anti-NTNG1 autoantibodies, and consequently detection of the biomarker-antibody complex between the NTNG1 polypeptide or one or more anti-NTNG1 antibody-binding fragments thereof and anti-NTNG1 autoantibodies.

Detection may be either qualitative or quantitative. Methods for labeling biological molecules such as antibodies are well-known in the art. The most commonly used detectable moieties in immunoassays are enzymes and fluorophores. In the case of an enzyme immunoassay (EIA or ELISA), an enzyme such as horseradish peroxidase, glucose oxidase, beta-galactosidase, alkaline phosphatase, and the like, is conjugated to the second antibody, generally by means of glutaraldehyde or periodate. The substrates to be used with the specific enzymes are generally chosen for the production of a detectable color change, upon hydrolysis of the corresponding enzyme. In the case of immunofluorescence, the second antibody is chemically coupled to a fluorescent moiety without alteration of its binding capacity. After binding of the fluorescently labeled antibody to the biomarker-antibody complex and removal of any unbound material, the fluorescent signal generated by the fluorescent moiety is detected, and optionally quantified. Alternatively, the secondary antibody may be labeled with a radioisotope, a chemiluminescent moiety, or a bioluminescent moiety.

Thus, the presence of an antibody may be determined in a qualitative or a quantitative manner. In a preferred embodiment, the term "detecting in a quantitative manner", as used herein, means that not only the presence of an antibody is detected, but that a result is obtained that includes information regarding the absolute or relative amount of the antibody in the sample.

In a more preferred embodiment, a value representing an absolute concentration is obtained. In another more preferred embodiment, a value representing a relative concentration or change of concentration is obtained. In another preferred embodiment, also referred to as "semi-quantitative" approach, the concentration of the antibody is placed in one of several groups, most preferably a concentration window meaning that it is virtually absent, a concentration window meaning that a borderline result is obtained and a concentration window meaning that the antibody is present. A further distinction into categories such as "weak positive" or "strong positive" signal is possible.

In general, obtaining a positive result using at least one detection method, such as described herein or known in the art, such as ELISA or immunofluorescence, preferably indirect immunofluorescence, when determining the presence of an anti-NTNG1 antibody in a sample from a subject such as a patient is sufficient to indicate the presence of said antibody. In one embodiment, in case that a respective analysis using a certain detection method, such as ELISA, would indicate the presence of an anti-NTNG1 antibody in a given sample, while another detection method would give a negative result, the sample would be regarded as comprising an anti-NTNG1 antibody. In one embodiment, the presence of an anti-NTNG1 antibody in a sample obtained from a subject indicates that the subject suffers or is likely to suffer in the present, past or future from a disease as described herein. In another embodiment, the presence of an anti-NTNG1 antibody in a sample obtained from a subject indicates that the subject has an increased risk to suffer from or to develop such a disease in the past, present or future.

In a preferred embodiment, the presence of an anti-NTNG1 antibody in a sample from a subject is determined using ELISA. In another preferred embodiment, the presence of an anti-NTNG1 antibody in a sample from a subject is determined using immunofluorescence, preferably indirect immunofluorescence.

The methods described herein for determining the presence of an anti-NTNG1 antibody in a sample can be combined with methods for determining the presence of other autoantibodies, the presence of which is associated with the occurrence of the diseases described herein or of similar diseases. For example, an NTNG1 polypeptide or fragment thereof, as described herein, can be used in conjunction with one or more polypeptides or fragments thereof binding to other autoantibodies, the presence of which is associated with the occurrence of the diseases described herein or of similar diseases. For example, a device comprising a NTNTG1 polypeptide or fragment thereof, such as the device of the present invention, may comprise further polypeptides or fragments thereof binding to other autoantibodies, the presence of which is associated with the occurrence of the diseases described herein or of similar diseases. Such device may be used to analyze a sample from a subject such as a patient for the presence of any autoantibody, the presence of which is associated with the occurrence of the diseases described herein or of similar diseases. In the case that a method using such a device or using several devices, wherein each device comprises at least one polypeptide or fragment thereof binding to an anti-NTNG1 antibody or to another antibody, preferably autoantibody, the presence of which is associated with the occurrence of the diseases described herein or of similar diseases, determining the presence of any antibody binding to any of the assayed polypeptides or fragments thereof may be sufficient for a skilled person to conclude on the presence of a certain disease or to limit the suspected disease to certain diseases or to aid in the diagnosis of a disease, as described herein, or to gain information about the risk of a subject to suffer in the present, past or future from or to develop a disease as described herein. Thus, under certain circumstances, it may be sufficient to determine the presence of either an anti-NTNG1 antibody or of any other autoantibody, the presence of which is associated with the occurrence of the diseases described herein or of similar diseases, without getting information or reaching a conclusion which specific antibody is present in a given sample. Consequently, determining the presence of an anti-NTNG1 antibody may comprise determining the presence of any antibody, preferably autoantibody, the presence of which is associated with the occurrence of the diseases described herein or of similar diseases.

A person skilled in the art will understand that under certain circumstances, it may be instrumental to first analyze the clinical symptoms of a patient having or suspected of having a disease which is associated with the presence of an anti-NTNG1 antibody. Depending on the symptoms, grade of impairment and other factors known in the art, a clinician or another medical or scientific personal may then determine whether the antibody titer of the subject to be analyzed is increased compared to a healthy subject or compared to the titer of the subject to be analyzed prior to the onset of symptoms or compared to the average. Subsequently or independently, one or more methods as described herein for determining the presence of an anti-NTNG1 antibody may be conducted to determine the presence of such antibody and/or to determine the presence of any antibody, the presence of which is associated with a disease as described herein. Thus, determining the presence of an anti-NTNG1 antibody may be used as a preinvestigation or as one investigation amongst others allowing a clinician to reach a conclusion whether or not a subject suffers or is likely to suffer in the present, past or future from a disease. Determining the presence of an anti-NTNG1 antibody may also be used to distinguish between drug or alcohol use or abuse or the presence of an infectious disease and the presence of an autoimmune disease, as described herein.

In certain embodiments, it may be instrumental to determine the Ig class of an anti-NTNG1 antibody, Thus, in one embodiment, determining the presence of an anti-NTNG1 antibody comprises determining the Ig class of said antibody. In other embodiments, determining the presence of an anti-NTNG1 antibody does not comprise determining the Ig class of said antibody. Likewise, determining the presence of an anti-NTNG1 antibody of a certain Ig class comprises determining the presence of anti-NTNG1 antibodies of other Ig classes. Determining the presence of an anti-NTNG1 antibody of a certain Ig class may also comprise determining the absence of said antibody.

Another method of the invention concerns the correlation between the presence and level of anti-NTNG1 autoantibodies and effectiveness of treatment, remission or relapse of patients with MGN, more specifically idiopathic MGN.

Current treatments used for membranous nephropathy, particularly idiopathic membranous nephropathy, are immunosuppressive therapy, for example, glucocorticoids, cyclosporin, tacrolimus, azathioprine, infliximab, omalizumab, daclizumab, adalimumab, eculizumab, efalizumab, natalizumab, omalizumab and rapamycin. It also includes cyclophosphamide, chlorambucil, and rituximab.

Thus, the invention further relates to an in vitro method of determining the effectiveness of a treatment for MGN in a subject, comprising (i) determining the level of anti-NTNG1 autoantibodies in a first biological sample obtained from a subject at a first time-point and (ii) determining the level of anti-NTNG1 autoantibodies in a second biological sample obtained from a subject at a second time-point, wherein a decrease in the level of anti-NTNG1 autoantibodies in the second time point compared to the first time point indicates that the treatment is effective, and/or an increase in the level of anti-NTNG1 autoantibodies in the second time point compared to the first time point indicates that the treatment is not effective.

In one embodiment, determining the level of anti-NTNG1 autoantibodies in a first or second sample comprises contacting a biological sample obtained from the subject with a Netrin G1 (NTNG1) polypeptide or one or more anti-NTNG1 antibody-binding fragments thereof and detecting any antigen-antibody complexes formed between the NTNG1 polypeptide or one or more anti-NTNG1 antibody-binding fragments thereof and anti-NTNG1 autoantibodies in the biological sample.

In one embodiment, the second time point is chosen later than the first time point, preferably at least 1 months, 2 months, 4 months, 6 months, 12 months, 24 months, 36 months later or more than 36 months later. The method can be performed several times using more than one first and second time points. In one embodiment, the method is performed in intervals ranging between 2 months and 24 months.

Preferably, the method of determining the effectiveness of a treatment for MGN in a subject is performed for subjects that have been diagnosed for MGN and that are NTNG1-positive subjects.

The level of the anti-NTNG1 autoantibodies can be detected by an immunoassay wherein an antigen-antibody complex is formed, as described above.

Upon treatment, for example, with immunosuppressive therapy, a decrease of the amount of detectably circulating anti-NTNG1 autoantibodies is observed or likely observed in case of effective treatment.

The treatment is considered to be effective when a decrease of at least 10%, at least 20%, at least 30%, at least 40%, at least 50%, at least 60%, at least 70%, or at least 80%, of the level of anti-NTNG1 autoantibodies is observed. Particularly, the treatment is considered to be effective when a decrease of at least 50% of the level of anti-NTNG1 autoantibodies is observed. In one embodiment, the treatment is considered to be effective when a decrease of between 10% to 100% of the level of anti-NTNG1 autoantibodies is observed. Hence, in some embodiments, the level of anti-NTNG1 autoantibodies after treatment is not detectable, i.e. 100% decreased.

Conversely, the treatment is considered to be ineffective or likely ineffective when level between the first and the second time point is stable or increases.

In one embodiment, the NTNG1 polypeptide or one or more anti-NTNG1 antibody-binding fragments thereof are soluble. In another embodiment, the NTNG1 polypeptide or one or more anti-NTNG1 antibody-binding fragments thereof are immobilized on a solid surface.

In one embodiment, the NTNG1 polypeptide or one or more anti-NTNG1 antibody-binding fragments thereof are isolated and/or recombinant.

NTNG1 Expression in Subjects with MGN

Furthermore, the inventors found that levels of NTNG1 polypeptides or one or more fragments thereof in the biological sample of a subject can be used to make a prognosis and/or diagnosis and/or determine the therapeutic needs in said subjects. Typically, NTNG1 polypeptides or one or more fragments thereof comprise at least one NTNG1 antigen that binds to circulating anti-NTNG1 autoantibodies of subjects with MGN.

Thus, a further aspect of the invention relates to an in vitro method for prognosis and/or diagnosis of MGN in a subject, comprising the steps of determining the expression level of NTNG1 polypeptide or one or more anti-NTNG1 antibody-binding fragments thereof in a biological sample obtained from said subject and comparing said expression level to a reference expression level, wherein an increased expression level of NTNG1 polypeptide or one or more anti-NTNG1 antibody-binding fragments thereof compared to said reference expression level is indicative of MGN.

In one embodiment, the biological sample is a tissue sample, preferably a renal biopsy sample. In one embodiment, the expression level of NTNG1 polypeptide or one or more anti-NTNG1 antibody-binding fragments thereof is measured in podocytes and/or in the glomerular basement membrane (GBM). In a preferred embodiment, an increased expression level of NTNG1 polypeptide or one or more anti-NTNG1 antibody-binding fragments thereof in podocytes and/or GBM of said subject compared to said reference expression level is indicative of MGN.

In one embodiment, the accumulation of the NTNG1 polypeptide along the capillary wall is indicative of MGN.

Thus in a specific embodiment, an increased expression level of NTNG1 polypeptide or one or more anti-NTNG1 antibody-binding fragments thereof in podocytes and/or GEM of said subject compared to said reference expression level in combination with the accumulation of the NTNG1 polypeptide along the capillary wall is indicative of MGN.

In one embodiment, the expression level of NTNG1 polypeptide or one or more anti-NTNG1 antibody-binding fragments thereof in a biological sample is determined by contacting the biological sample with an anti-NTNG1 antibody or one or more antigen-binding fragments thereof.

In one embodiment, the anti-NTNG1 antibody comprises a full-length antibody or one or more antibody fragments capable of binding to one or more NTNG1 antigens.

"Antibodies" or "antibody", also called "immunoglobulins" (Ig), generally comprise four polypeptide chains, two heavy (H) chains and two light (L) chains, and are therefore multimeric proteins, or comprise an equivalent Ig homologue thereof (e.g., a camelid antibody comprising only a heavy chain, single-domain antibodies (sdAb) or nanobodies which can either be derived from a heavy or a light chain).

The term "antibodies" as used herein includes antibody-based binding proteins or fragments thereof, or modified antibody formats, all of which retain their antigen target-binding capacity. The term "antibodies" also includes full length functional mutants, variants, or derivatives thereof (including, but not limited to, murine, chimeric, humanized and fully human antibodies) which retain the essential epitope binding features of an Ig molecule, and includes dual specific, bispecific, multispecific, and dual variable domain Igs. Ig molecules can be of any class (e.g., IgG, IgE, IgM, IgD, IgA, and IgY), or subclass (e.g., IgG1, IgG2, IgG3, IgG4, IgA1 and IgA2) and allotype. Ig molecules may also be mutated e.g. to enhance or reduce affinity for Fcγ receptors or the neonatal Fc receptor (FcRn).

An "antibody fragment", as used herein, relates to a molecule comprising at least one polypeptide chain derived from an antibody that is not full length and exhibits antigen target binding, including, but not limited to (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region (reduction of a F(ab')2 fragment result in two Fab' fragment with a free sulfhydryl group); (iii) a heavy chain portion of a Fab (Fa) fragment, which consists of the VH and CH1 domains; (iv) a variable fragment (Fv) fragment, which consists of the VL and VH domains of a single arm of an antibody; (v) a domain antibody (dAb) fragment, which comprises a single variable domain; (vi) an isolated complementarity determining region (CDR): (vii) a single chain Fv fragment (scFv); (viii) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites; (ix) a linear antibody, which comprises a pair of tandem Fv segments (VH-CH1-VH-CH1) which, together with complementarity light chain polypeptides, form a pair of antigen binding regions; (x) Dual-Variable Domain Immunoglobulin (xi) other non-full length portions of immunoglobulin heavy and/or light chains, or mutants, variants, or derivatives thereof, alone or in any combination.

A "nanobody" or "single-domain antibody" or "sdAb" is an antibody fragment consisting of a single monomeric variable antibody domain and is able to bind selectively to a specific antigen. Nanobodies typically comprise one variable domain of a heavy-chain ($V_H$). They are often derived from immunization of dromedaries, camels, llamas, alpacas or sharks, who naturally produce single domain $V_{HH}$ antibodies.

An "aptamer" is an oligonucleotide or peptide molecule that can bind to a specific target molecule. Aptamers can be used instead of antibodies and exhibit high binding affinity.

In one embodiment, the antigen-binding fragments of the anti-NTNG1 antibody are not full length antibodies and are selected from the group consisting of a F(ab) fragment, a F(ab')2 fragment, a heavy chain portion of a Fab (Fa) fragment, a variable fragment (Fv) fragment, a domain antibody (dAb), an isolated complementarity determining region (CDR), a single chain Fv fragment (scFv), a diabody, a single domain antibody (sdAb) or nanobody, a linear antibody, Dual-Variable Domain Immunoglobulin, and aptamer, or other non-full length portions of immunoglobulin heavy and/or light chains, or mutants, variants, or derivatives thereof, alone or in any combination. In a preferred embodiment, the antigen-binding fragments of the anti-NTNG1 antibody are selected from F(ab) fragment, F(ab')2 fragment, nanobody and aptamer.

In one embodiment, the anti-NTNG1 antibody is a monoclonal antibody, a polyclonal antibody or an aptamer. In a preferred embodiment, the anti-NTNG1 antibody is a monoclonal antibody.

In this case, the endogenous expression of antigen-comprising NTNG1 polypeptide serves as a biomarker. In one embodiment, the expression level of NTNG1 polypeptide or one or more anti-NTNG1 antibody-binding fragments thereof in a biological sample is increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% compared to the reference expression level. In a preferred embodiment, the expression level of NTNG1 polypeptide or one or more anti-NTNG1 antibody-binding fragments thereof in a biological sample is increased by at least 50% compared to the reference expression level. In some embodiments, the expression level of NTNG1 polypeptide or one or more anti-NTNG1 antibody-binding fragments thereof in a biological sample is increased by more than 100%, more than 200%, more than 300%, more than 400% or more than 500% compared to the reference expression level. In some embodiments, the expression level of NTNG1 polypeptide or one or more anti-NTNG1 antibody-binding fragments thereof in a biological sample is increased by 5% to 500%, preferably by 50% to 500%, more preferably by 50% to 200% compared to the reference expression level. In one embodiment, said expression level refers to the expression level in podocytes and/or GBM.

In one embodiment, the reference expression level is determined by determining the expression level of NTNG1 polypeptide or one or more anti-NTNG1 antibody-binding fragments thereof in a group of subjects without NTNG1-associated MGN and calculating the mean expression level of NTNG1 polypeptide or one or more anti-NTNG1 antibody-binding fragments thereof in subjects without NTNG1-associated MGN. In one embodiment, said expression level refers to the expression level in podocytes and/or GBM.

Additionally, the expression level of the NTNG1 polypeptide or one or more anti-NTNG1 antibody-binding fragments thereof may also be measured on the basis of RNA. Hence, in one embodiment, the level of NTNG1 polypeptide or one or more anti-NTNG1 antibody-binding fragments thereof in a biological sample is determined by measuring the level of NTNG1 mRNA or detectable fragments thereof in a biological sample from a subject.

In one embodiment, the mRNA or fragments thereof are between 20 and 2000 nucleotides in length. In one embodiment, mRNA or fragments thereof are at least 10, at least 20, at least 30, at least 40, at least 50, at least 60, at least 70, at least 80, at least 90, at least 100, at least 150, at least 200, at least 250, at least 300, at least 350, at least 400, at least 450 or at least 500 nucleotides in length.

mRNA or fragments thereof can be detected using known methods such as polymerase chain reaction (PCR), quantitative PCR, RNA in situ hybridization, enzymatic digest, agarose gel-electrophoresis, expression profiling, RNA sequencing and next-generation sequencing, or Northern blotting.

In one embodiment, oligonucleotide primers are used to determine the level of NTNG1 mRNA expression in a biological sample from a subject. The oligonucleotide primers comprise at least 12 consecutive nucleotides selected from the nucleotide sequence according to SEQ ID NO: 4 or its reverse compliment sequence. In one embodiment, the oligonucleotide primers comprise at least 12, at least 15, at least 18 or at least 20 consecutive nucleotides selected from the nucleotide sequence according to SEQ ID NO: 4 or its reverse compliment sequence.

Methods of determining expression level of nRNA are well known in the field and may include transcribing RNA from a sample to cDNA by a reverse transcriptase, followed by second strand synthesis and polymerase chain reaction. These steps may be performed in one reaction setup or sequentially, mRNA expression levels can also be determined using sequencing methods such as RNAseq or next generation sequencing. In one embodiment, the expression level of NTNG1 polypeptide or one or more anti-NTNG1 antibody-binding fragments thereof is determined by quantitative polymerase chain reaction (qPCR).

In a further aspect, the invention also provides a kit for diagnosing and/or prognosing MGN in a subject, the kit comprising (i) an NTNG1 polypeptide or one or more anti-NTNG1 antibody-binding fragments thereof and (ii) a reagent for detection of an antigen-antibody complex formed between the NTNG1 polypeptide or one or more anti-NTNG1 antibody-binding fragments thereof and one or more anti-NTNG1 autoantibody present in the sample.

In one embodiment, the kit further comprises a solid surface on which the NTNG1 polypeptide or one or more anti-NTNG1 antibody-binding fragments thereof is immobilized, preferably wherein the solid surface is an array, a microchip, a microplate, a bead, a resin, a membrane or a column. The beads are preferably magnetic beads or agarose beads. In a preferred embodiment, the kit comprises the device of the present invention, wherein the device comprises the solid surface.

In one embodiment, NTNG1 polypeptide or one or more anti-NTNG1 antibody-binding fragments thereof contains at least one NTNG1 antigen that binds to circulating anti-NTNG1 autoantibodies of subjects with MGN. In another embodiment, the NTNG1 antigen comprises at least one epitope that is recognized by circulating anti-NTNG1 autoantibodies of subjects with MGN.

In one embodiment, the biological sample is a blood sample or a urine sample. Preferably, the biological sample is a blood sample, more preferably a serum sample. In another embodiment, the sample is a tissue sample, preferably a renal biopsy sample. Hence, in one embodiment, the biological sample is a blood sample or a renal biopsy sample. Preferably, the biological sample is a blood sample.

Another aspect of the invention relates to an in vitro method of diagnosing membranous glomerulonephritis (MGN) in a subject, comprising contacting a biological sample from the subject with one or more of an PLA2R1 polypeptide or one or more anti-PLA2R1 antibody-binding fragments thereof, an THSD7A polypeptide or one or more anti-THSD7A antibody-binding fragments thereof and an NTNG1 polypeptide or one or more anti-NTNG1 antibody-binding fragments thereof. In one embodiment, the contacting is performed consecutively.

The contacting can also be performed simultaneously. In a particular embodiment, the different polypeptides or one or more antibody-binding fragments thereof are labelled with different detectable moieties. Therefore, they can be contacted simultaneously.

In one embodiment, the PLA2R1 polypeptide comprises an amino acid sequence that is at least 70% identical to the amino acid sequence according to SEQ ID NO: 9. In another embodiment, the PLA2R1 polypeptide comprises an amino acid sequence that is at least 75%, at least 80%, at least 85%, at least 90%, at least 95%, at least 98%, at least 99% or 100% identical to the amino acid sequence according to SEQ ID NO: 9.

In one embodiment, said anti-PLA2R1 antibody-binding fragment of the PLA2R1 polypeptide comprises at least 10 consecutive amino acids of the entire amino acid sequence of PLA2R1. In another embodiment, said anti-PLA2R1 antibody-binding fragment of PLA2R1 comprises at least 20, at least 40, at least 60, at least 80, at least 100, at least 120, at least 140, at least 160, at least 180, at least 200, at least 250, at least 300, at least 350, at least 400, at least 450, at least 500 or 539 consecutive amino acids of the entire amino acid sequence of full-length PLA2R1 (SEQ ID NO: 9).

In another embodiment, the anti-PLA2R1 antibody-binding fragment of PLA2R1 comprises at least 5%, at least 10%, at least 20%, at least 30%, at least 40%, at least 50%, at least 60%, at least 70%, at least 75%, at least 80%, at least 85%, at least 90%, at least 95%, at least 98%, at least 99% or 100% of the amino acid sequence of full-length PLA2R1, i.e. SEQ ID NO: 9.

Preferably, the anti-PLA2R1 antibody-binding fragment of PLA2R1 is recognized by an autoantibody directed against PLA2R1.

In one embodiment, the THSD7A polypeptide comprises an amino acid sequence that is at least 70% identical to the amino acid sequence according to SEQ ID NO: 10. In another embodiment, the THSD7A polypeptide comprises an amino acid sequence that is at least 75%, at least 80%, at least 85%, at least 90%, at least 95%, at least 98%, at least 99% or 100% identical to the amino acid sequence according to SEQ ID NO: 10.

In one embodiment, said anti-THSD7A antibody-binding fragment of the THSD7A polypeptide comprises at least 10 consecutive amino acids of the entire amino acid sequence of THSD7A. In another embodiment, said anti-THSD7A antibody-binding fragment of THSD7A comprises at least 20, at least 40, at least 60, at least 80, at least 100, at least 120, at least 140, at least 160, at least 180, at least 200, at least 250, at least 300, at least 350, at least 400, at least 450, at least 500 or 539 consecutive amino acids of the entire amino acid sequence of full-length THSD7A (SEQ ID NO: 10).

Table 1. Table 1 also shows a comparison between the "Gentle" Western Blot protocol used for the antigens of the invention and a standard protocol published by BioRad (BioRad Bulletin #6211 "Transfer Buffer Formulations, Ver B", BioRad "Mini-PROTEAN® TGX™ Precast Gels Quick Start Guide").

TABLE 1

Comparison of "Gentle" Western Blot and standard Western Blot

|  | "Gentle" Western Blot | Standard Western Blot protocol according to BioRad |
|---|---|---|
| SDS-PAGE: | | |
| Sample buffer | 1 × Laemmli sample buffer without reducing agent | 1 × Laemmli sample buffer with or without reducing agent |
| Boiling of sample | No | Yes, 90-100° C., 5 min |
| Gel | Mini-Protean® TGXTM Precast Gel | |
| Running buffer | 25 mM Tris-Base 192 mM glycine 0.025% SDS pH 8.3 | 25 mM Tris-Base 192 mM glycine 0.1% SDS pH 8.3 |
| Voltage | 80-100 V | 200 V |
| Running time | 60-80 min | 30-40 min |
| Transfer: | | |
| System | Biorad Mini Trans-Blot® cell on PVDF membrane | |
| Transfer buffer | 25 mM Tris-Base 192 mM glycine 5% methanol pH 8.3 | 25 mM Tris-Base 192 mM glycine 20% methanol pH 8.3 |
| Equilibration time of gel in transfer buffer | 5 min | 15 min |
| Temperature control | Trans-Blot® cell placed in ice bath ("Tank-Blot") | cold pack placed in Trans-Blot® cell ("semi-dry") |
| Voltage | 12 V at maximum 25 mA | 100 V |
| Transfer time | 3 h | 30-60 min |
| Immunodetection | all incubation and washing steps performed at 4° C. | |

SDS = sodium dodecyl sulphate, PVDF = Polyvinylidene fluoride

In another embodiment, the anti-THSD7A antibody-binding fragment of THSD7A comprises at least 5%, at least 10%, at least 20%, at least 30%, at least 40%, at least 50%, at least 60%, at least 70%, at least 75%, at least 80%, at least 85%, at least 90%, at least 95%, at least 98%, at least 99% or 100% of the amino acid sequence of full-length THSD7A, i.e. SEQ ID NO: 10.

Preferably, the anti-THSD7A antibody-binding fragment of THSD7A is recognized by an autoantibody directed against THSD7A.

EXAMPLES

Example 1: Comparison of "Gentle" Western Blot and Standard Western Blot

The epitopes recognized by autoantibodies in MGN associated with PLA2R1 and THSD7A are conformation-dependent and can only be detected by Western Blot performed under non-reducing conditions. It was hypothesized that the same would be true for the new target antigen. Additionally, it was advantageous to perform the protein transfer after polyacrylamide gel-electrophoresis using a "Tank-Blot" method, as opposed to the more commonly used "semi-dry" transfer method. Performing a semi-dry transfer led to loss of circulating antibody binding (see FIG. 1B). SDS-PAGE and Western Blot were performed according to the specifically developed "Gentle" Western Blot protocol detailed in Table 1.

Figure 2A:
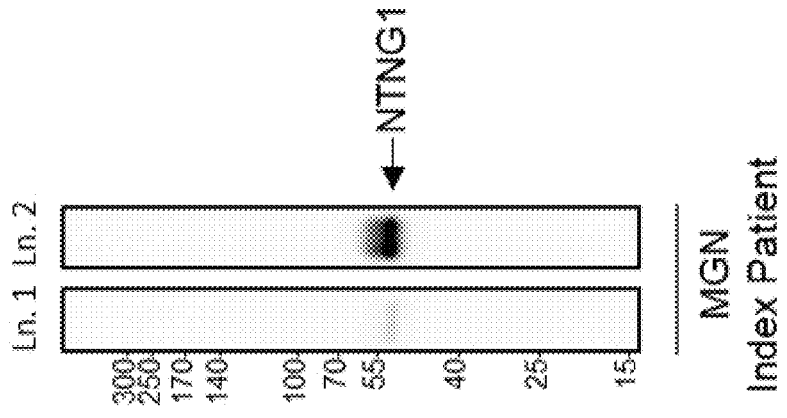
FIG. 2A: Comparison of antibody binding to target antigen after protein transfer using "Semi-dry", Ln. 1 (25 V, 1 A, 30 min at room temperature) or "Tank-Blot" method, Ln. 2 (12 V, 25 mA, 3 h on ice). Except for the transfer method, all procedural conditions were kept the same. The protein sample is human glomerular extract (HGE) which was separated in a polyacrylamide gel by electrophoresis (SDS-PAGE). Recognition of PLA2R1 target antigen by PLA2R1-antibody positive patient serum.
Figure 2B:
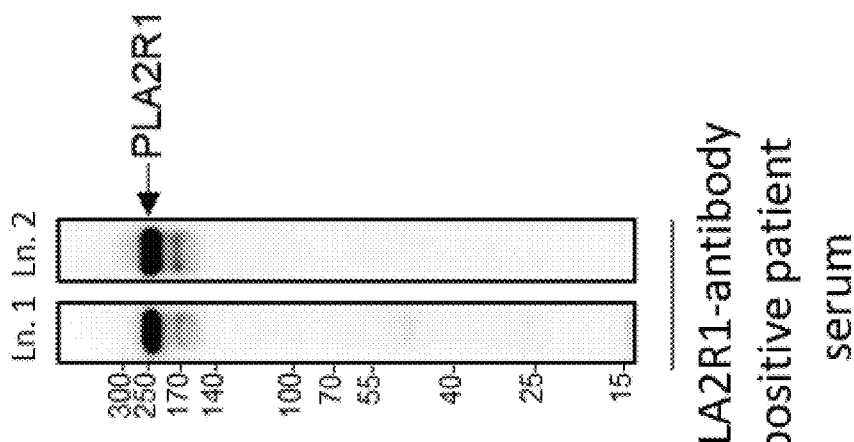
FIG. 2B: Comparison of antibody binding to target antigen after protein transfer using "Semi-dry", Ln. 1 (25 V, 1 A, 30 min at room temperature) or "Tank-Blot" method. Ln. 2 (12 V. 25 mA, 3 h on ice). Except for the transfer method, all procedural conditions were kept the same. The protein sample is human glomerular extract (HGE) which was separated in a polyacrylamide gel by electrophoresis (SDS-PAGE). Recognition of NTNG1 target antigen by MGN index patient serum.

SDS-PAGE of human glomerular extract (HGE) proteins followed by Western blot was performed using either the "semi-dry" or "Tank-Blot" method of transfer. FIG. 2A shows blotting of PLA2R1-antibody positive patient serum on HGE. Recognition of PLA2R1 by the PLA2R1-antibody positive patient serum occurs in both conditions. FIG. 2B shows blotting of MGN index patient serum on HGE. Recognition of NTNG1 by the NTNG1-antibody positive serum of the MGN index patient is significantly improved by the "Tank-Blot" transfer method.

Example 2: Identification of Novel Target Antigen

Serum samples were taken from a cohort of 406 patients with known MGN confirmed by renal biopsy. Sera were tested for serum anti-PLA2R1 and/or anti-THSD7A autoantibodies using ELISA and an indirect immunofluorescence test. 319 patients (79%) were positive for PLA2R1 and/or THSD7A antibodies. The sera of the remaining 87 patients were further investigated.

The procedure used to identify novel target antigens for MGN is summarized in FIG. 1. The procedure to identify novel target antigens in these sera comprises the following steps:

Step 1; Identification of IgG4-Specific Recognition in the Membrane Fraction of Human Glomerular Extract Using Non-Reducing Western Blot a) Sample Preparation Human glomeruli were collected by sieving as previously reported (Tomas et al., NEJM, 2014), flash frozen in liquid nitrogen and stored at −80° C. until use. For the preparation of human glomeruli extracts a glomeruli pellet was resuspended in extraction buffer 1 (100 mM Tris pH 8.0, 20% glycerol, supplemented with 1×EDTA-free protease inhibitor). The glomeruli were ruptured by sonication using 5× 10 s pulses with 10% power. Solubilization of the membrane fraction was initiated by addition of 0.5% Triton X-100 or 0.5% Lauryl Maltose Neopentyl Glycol (LMNG), followed by incubation for 1 h at 4° C. on a rotator. The non-solubilized fraction was removed by centrifugation for 10 min at 14,800×g. The supernatant was collected and applied to Protein G resin, which was pre-equilibrated with extraction buffer I, followed by incubation at 4° C. for 2 h on a rotator. The supernatant was applied to a Spin-X column and centrifuged for 2 min at 16,000×g. The flow-through fraction was collected and presents the HGE fraction.

For preparation of the HGE-membrane and HGE-cytoplasm fraction a similar procedure was applied, with the following modifications. Directly after sonication the sample was centrifuged for 15 min at 20,000×g at 4° C., The supernatant was collected and presents the HGE-cytoplasm fraction. The pellet was resuspended in extraction buffer II (100 mM Tris pH 8.0, 10% glycerol, supplemented with 1×EDTA-free protease inhibitor) and the centrifugation step was repeated. The supernatant was discarded. The pellet was resuspended in extraction buffer I supplemented with 0.5% LMNG and was incubated for 30 min at 4° C. on a rotator. The centrifugation step was repeated. The collected supernatant was applied to protein G resin, which was equilibrated in extraction buffer. The samples were incubated for 2 h at 4° C. on a rotator. The supernatant was applied to a Spin-X filter and centrifuged for 2 min at 16,000×g. The flow-through fraction was collected and presents the HGE-membrane fraction. All samples were flash frozen in liquid nitrogen and stored at −80° C. until use.

b) Western Blot

HGE proteins were separated according to size using SDS-PAGE (sodium dodecyl sulphate-polyacrylamide gel electrophoresis) and transferred to a methanol activated PVDF membrane according to the "Gentle" Western Blot protocol described herein. Since HGE comprises the proteins usually expressed in the glomeruli of the kidney, it most likely contains proteins that elicit auto-antibody responses in MGN. Hence, when the MGN patient sera are blotted against the HGE proteins, the resulting positive signals derive from circulating antibodies comprised in the patient sera binding to antigens comprised in HGE proteins.

HGE protein samples containing only HGE membrane fraction proteins (HGE-membrane) or only cytosolic fraction proteins (HGE-cytoplasm) were used. Furthermore, a sample of deglycosylated HGE proteins was also tested. Mouse anti-human IgG4 Fc-HRP is used as a secondary antibody in order to detect binding of circulating IgG4 antibodies on the blot (Southern Biotech 9200-05).

Patient sera that showed specific IgG4 activity against HGE membrane proteins, but not cytosolic proteins, were selected for further study. The serum of a healthy subject was used as a control sample.

Step 2: Purification of IgG4 from the Index-Patient Using Affinity Chromatography Next, the circulating IgG4 antibodies were extracted from the patient sera. To this end, the IgG4 were purified using affinity chromatography (CaptureSelect™ IgG4 (Hu) Affinity Matrix ThermoScientific, #290005) according to the manufacturer's instructions, Before neutralization, the eluted antibodies were applied to a Spin-X filter and centrifuged for 2 min at 16,000×g. The flow-through fraction was neutralized using neutralization buffer (1 M Tris pH 8.5). The purified IgG4 was concentrated using Spin-X® UF 500 columns at 4° C. and 10,000×g. A buffer exchange was performed to the Dynabeads™ C1 buffer using the same ultrafiltration setup.

Step 3: Covalent Coupling of IgG4 to Magnetic Beads

In this step, the purified patient IgG4 antibodies from step 2 were coupled to epoxy-coated magnetic beads (Dynabeads™ M270 Epoxy) according to the manufacturers instructions. The surface epoxy groups covalently bind primary amino and sulfhydryl groups and are commonly used for coupling antibodies to magnetic beads. To remove access of uncoupled antibody, the resin was additionally washed with Pierce™ IgG elution buffer supplemented with 0.5% LMNG.

Step 4a: Immunoprecipitation of Membrane Fraction from Human Glomerular Extract and Elution and Neutralization of the Precipitated Target Antigen Using the antibody-coupled magnetic beads as a capture ligand, the polypeptides or polypeptide fragments containing the target antigen for the specific IgG4 antibody were immunoprecipitated from the HGE-membrane fraction pool of proteins using the Dynabeads™ Co-Immunoprecipitation kit with the following modifications. After incubation with the HGE-membrane, four additional washing steps were performed using binding buffer (100 mM Tris-HCl pH 8.0, 10% glycerol, 1× protease inhibitor) supplemented with 250 mM NaCl, 500 mM NaCl, 250 mM NaCl and 0 mM NaCl, respectively. Further, the Dynabeads™ elution buffer was supplemented with 0.25% LMNG and 10% glycerol.

Step 5: Concentration of Target Antigen Using Ultrafiltration

The target antigen was concentrated by ultrafiltration using Microcon YM-10 columns following the manufactures instructions.

Step 6 (Optional): Validation Using Silver Staining of SOS-PAGE Gel

Optionally, the purified target antigen-containing polypeptide or fragment can be visualized on an SDS-polyacrylamide gel using silver staining (Pierce™ Silver Stain Kit) following the manufacturer's instructions. This method makes polypeptides visible within the gel by deposition of metallic silver onto the surface of the gel at the location of protein bands. Silver ions bind with protein functional groups such as carboxylic acid, imidazole, sulfhydryl and amines, Thus, this step can validate the presence of one or more polypeptides in the sample.

Step 7: Identification of Target Antigen Using Mass Spectrometry Analysis

Figure 3:
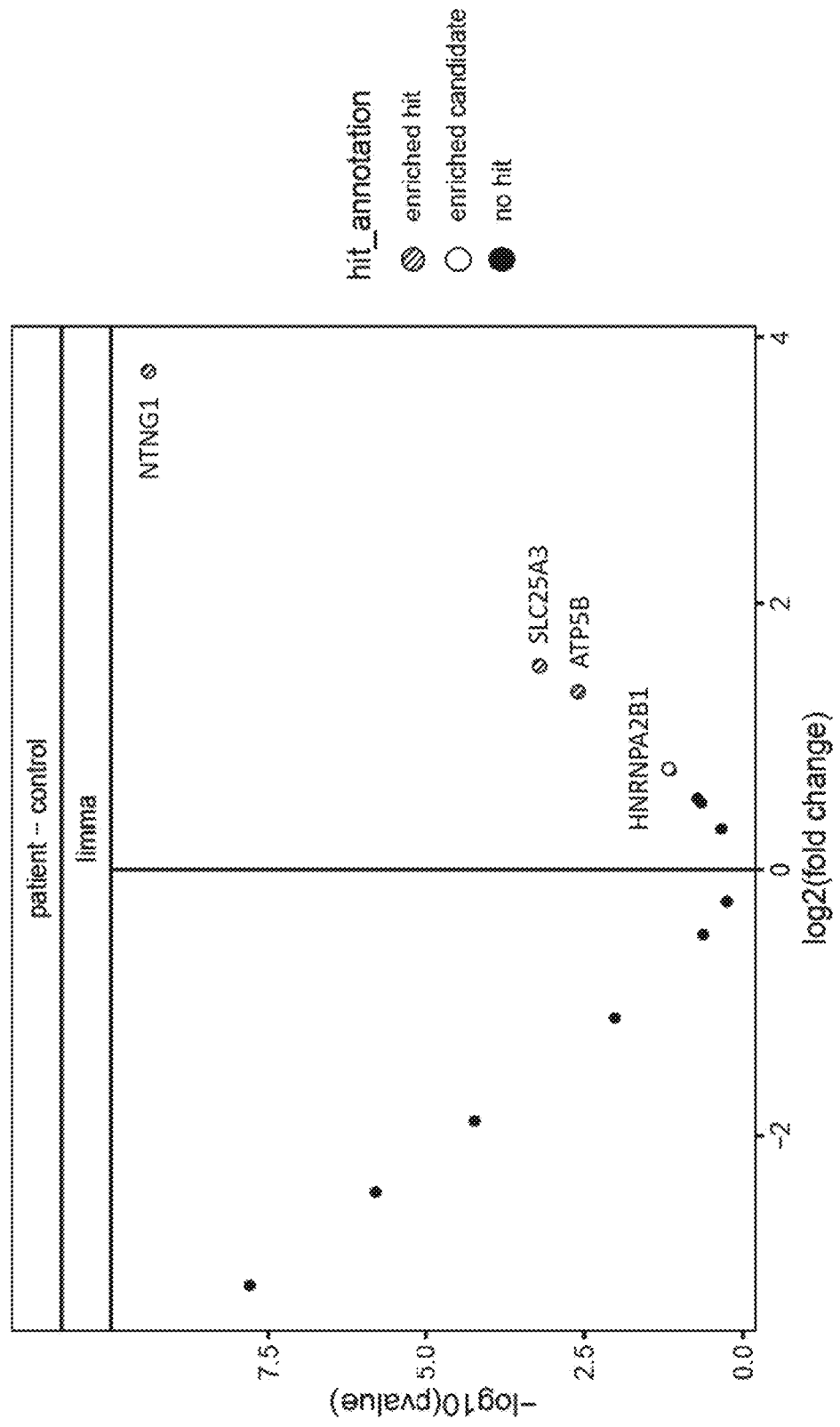
FIG. 3: Identification of NTNG1 as target antigen in the MGN index patient by tandem mass tagged (TMT)-based relative quantification mass spectrometry. Shown is a volcano blot showing the specific accumulation of NTNG1 in the patient sample compared to the healthy control.

The isolated target antigen was identified using mass spectrometry analysis. The mass spectrometry using tandem mass tagged (TMT)-based relative quantification showed a significant difference in the concentration of a specific protein in the patient serum compared to the control (FIG. 3). Hence, the antigen-containing protein was identified as Netrin G1 (NTNG1).

Step 8: Validation of Target Antigen Using Non-Reducing Western Blot

In order to confirm the presence of anti-NTNG1 antibodies in the serum of the index patient, a "Gentle" Western Blot was performed using HGE protein samples of HGE membrane fraction, HGE cytoplasmic fraction and deglycosylated HGE proteins. When probed with patient serum from the selected MGN index patient and a secondary anti-IgG4 antibody, a band was detected at about 50 kDa in the HGE membrane fraction, but not the HGE cytosolic fraction, which was also present after deglycosylation of proteins (FIG. 4A).

Figure 4D:
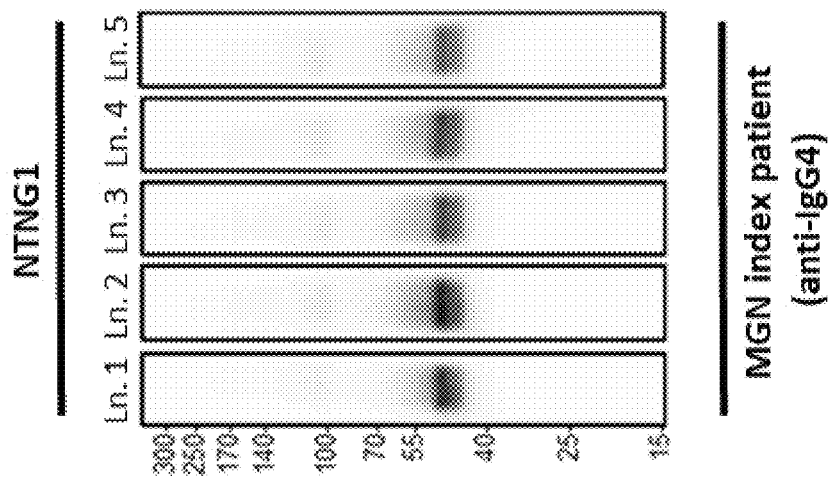
FIG. 4D: Validation of NTNG1 as target antigen in the MGN index patient. Gentle Western Blot of recombinantly expressed NTNG1 polypeptide probed with serum of the index patient at time of diagnosis (Ln. 1), +36 months (Ln. 2), +38 months (Ln, 3), +45 months (Ln. 4), and +48 months (Ln. 5) after diagnosis. Secondary antibody was anti-IgG4 antibody.
Figure 4C:
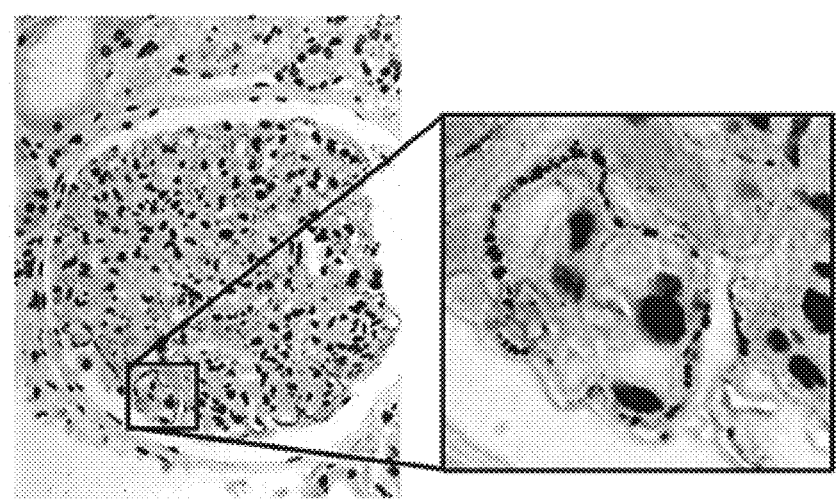
FIG. 4C: Validation of NTNG1 as target antigen in the MGN index patient. Immunohistochemical staining of renal biopsy sample from the MGN index patient with anti-NTNG1 antibody.

To validate the presence of anti-NTNG1 antibodies in the serum of the index patient, a "Gentle" Western Blot was performed using recombinantly expressed NTNG1 polypeptide (FIG. 4B). The serum of the MGN index patient reacted with the recombinant NTNG1, but not the sera of a healthy subject, PLA2R1-antibody positive patient or THSD7A-antibody positive patient. This shows that the serum of the MGN index patient comprises anti-NTNG1 antibodies.

Example 3: Immunohistochemical Characterization of MGN Index Patient

Immunohistochemical staining was performed on a kidney biopsy of the MGN index patient using an mouse monoclonal anti-NTNG1 antibody (SantaCruz; #sc-271774) following standard procedures (FIG. 40). The immunohistochemical staining shows positive signal for NTNG1 along the glomerular basement membrane, which is analogous to the localization of known MGN antigens and characteristic of the disease. Immunohistochemical staining with anti-PLA2R1 and anti-THSD7A antibodies did not show an increased expression of these proteins in the index patient, confirming that NTNG1, but not PLA2R1 or THSD7A acts as a disease-causing antigen.

Example 4: Presence of Anti-NTNG1 Antibodies in Patient Blood Over Time

Serum samples were collected from the MGN index patient at the time of diagnosis (time point 0) and at +36, +38, +45 and +48 months after diagnosis. Probing a "Gentle" Western Blot with recombinant NTNG1 polypeptide with these serum samples showed that the serum of this patient remained positive for circulating anti-NTNG1 antibodies over time. The expression of NTNG1 antigen and the presence of circulating anti-NTNG1 antibodies over time suggest that the anti-NTNG1 antibody level in patient serum can be used as a biomarker and to determine the effectiveness of a therapy in the patient. Furthermore, the therapy can be adapted to the level of anti-NTNG1 antibodies, which reflect the immunological activity of the disease.

The Invention is Further Described by the Following Items:
1. in vitro method, comprising detecting one or more autoantibodies recognizing a Netrin G1 (NTNG1) polypeptide or one or more antibody-binding fragments thereof in a biological sample obtained from a subject.
2. in vitro method according to item 1, wherein the in vitro method comprises the steps of
   (i) contacting a biological sample obtained from the subject with a Netrin G1 (NTNG1) polypeptide or one or more anti-NTNG1 antibody-binding fragments thereof, and
   (ii) detecting any antigen-antibody complexes formed between the NTNG1 polypeptide or one or more anti-NTNG1 antibody-binding fragments thereof and anti-NTNG1 autoantibodies.
3. in vitro method according to any of the preceding items, wherein detecting the antigen-antibody complexes between the NTNG1 polypeptide or one or more anti-NTNG1 antibody-binding fragments thereof and anti-NTNG1 autoantibodies comprises determining the presence of anti-NTNG1 autoantibodies, optionally wherein determining the presence of anti-NTNG1 autoantibodies comprises determining the level of anti-NTNG1 autoantibodies.
4. in vitro method of determining the effectiveness of a treatment for MGN in a subject, comprising
   (i) determining the level of anti-NTNG1 autoantibodies in a first biological sample obtained from a subject at a first time-point; and
   (ii) determining the level of anti-NTNG1 autoantibodies in a second biological sample obtained from a subject at a second time-point;
   wherein a decrease in the level of anti-NTNG1 autoantibodies in the second time point compared to the first time point indicates that the treatment is effective; and/or an increase in the level of anti-NTNG1 autoantibodies in the second time point compared to the first time point indicates that the treatment is not effective.
5. in vitro method according to item 4, wherein determining the level of anti-NTNG1 autoantibodies in a first or second sample comprises contacting a biological sample obtained from the subject with a Netrin G1 (NTNG1) polypeptide or one or more anti-NTNG1 antibody-binding fragments thereof and detecting any antigen-antibody complexes formed between the NTNG1 polypeptide or one or more anti-NTNG1 antibody-binding fragments thereof and anti-NTNG1 autoantibodies in the biological sample.
6. in vitro method according to any one of the preceding items, wherein the biological sample is a blood sample.
7. in vitro method for prognosis and/or diagnosis of MGN in a subject, comprising the steps of determining the expression level of NTNG1 polypeptide or one or more anti-NTNG1 antibody-binding fragments thereof in a biological sample obtained from said subject and comparing said expression level to a reference expression level, wherein an increased expression level of NTNG1 polypeptide or one or more anti-NTNG1 antibody-binding fragments thereof compared to said reference expression level is indicative of MGN.
8. in vitro method according to item 7, wherein the reference expression level is determined by
   (i) determining the expression level of NTNG1 polypeptide or one or more anti-NTNG1 antibody-binding fragments thereof in biological samples obtained from a group of subjects without NTNG1-associated MGN and/or a group of healthy subjects, and
   (ii) calculating the mean expression level of NTNG1 polypeptide or one or more anti-NTNG1 antibody-binding fragments thereof in said biological samples.
9. in vitro method according to items 7 or 8, wherein the biological sample is a tissue sample, preferably a renal biopsy sample.
10. Kit, optionally for detecting, diagnosing and/or prognosing MGN in a subject, the kit comprising (i) a protein including an NTNG1 polypeptide or one or more anti-NTNG1 antibody-binding fragments thereof and/or (ii) a reagent for detection of an antigen-antibody complex formed between the NTNG1 polypeptide or one or more anti-NTNG1 antibody-binding fragments thereof and one or more anti-NTNG1 autoantibodies present in the sample.
11. in vitro method according to any one of items 1-9 or kit according to item 10, wherein the NTNG1 polypeptide or one or more anti-NTNG1 antibody-binding fragments thereof are soluble.

12. in vitro method according to any one of items 1-9 or kit according to item 10, wherein the NTNG1 polypeptide or one or more anti-NTNG1 antibody-binding fragments thereof are isolated and/or recombinant.
13. In vitro method according to any one of items 1-9 or kit according to item 10, wherein the NTNG1 polypeptide or one or more anti-NTNG1 antibody-binding fragments thereof are immobilized on a solid surface, optionally wherein the solid surface is an array, a microchip, a microplate, a bead, a resin, a membrane or a column.
14. In vitro method according to any one of items 1-9 or kit according to item 10, wherein the NTNG1 polypeptide or one or more anti-NTNG1 antibody-binding fragments thereof are capable of binding to anti-NTNG1 antibodies.
15. A diagnostic device coated with an NTNG1 polypeptide or one or more anti-NTNG1 antibody-binding fragments thereof.
16. Use of an NTNG1 polypeptide or one or more antibody-binding fragments thereof for in vitro diagnosis of MGN,

```
Sequences
NTNG1-isoform-3
                                             SEQ ID NO: 1
MYLSRFLSIHALWVTVSSVMQPYPLVWGHYDLCKTQIYTEEGKVWDYMAC
QPESTDMTKYLKVKLDPPDITCGDPPETFCAMGNPYMCNNECDASTPELA
HPPELMFDFEGRHPSTFWQSATWKEYPKPLQVNITLSWSKTIELTDNIVI
TFESGRPDQMILEKSLDYGRTWQPYQYYATDCLDAFHMDPKSVKDLSQHT
VLEIICTEEYSTGYTTNSKIIHFEIKDRFAFFAGPRLRNMASLYGQLDTT
KKLRDFFTVTDLRIRLLRPAVGEIFVDELHLARYFYAISDIKVRGRCKCN
LHATVCVYDNSKLTCECEHNTTGPDCGKCKKNYQGRPWSPGSYLPIPKGT
ANTCIPSISSIGNCECFGHSNRCSYIDLLNTVICVSCKHNTRGQHCELCR
LGYFRNASAQLDDENVCIECYCNPLGSIHDRCNGSGFCECKTGTTGPKCD
ECLPGNSWHYGCQPNVCDNELLHCQNGGTCHNNVRCLCPAAYTGILCEKL
RCEEAGSCGSDSGQGAPPHGSPALLLLTTLLGTASPLVF NTNG1-isoform-3 aa 1-510
                                             SEQ ID NO: 2
MYLSRFLSIHALWVTVSSVMQPYPLVWGHYDLCKTQIYTEEGKVWDYMAC
QPESTDMTKYLKVKLDPPDITCGDPPETFCAMGNPYMCNNECDASTPELA
HPPELMFDFEGRHPSTFWQSATWKEYPKPLQVNITLSWSKTIELTONIVI
TFESGRPDQMILEKSLDYGRTWQPYQYYATDCLDAFHMDPKSVKDLSQHT
VLEIICTEEYSTGYTTNSKIIHFEIKDRFAFFAGPRLRNMASLYGQLDTT
KKLRDFFTVTDLRIRLLRPAVGEIFVDELHLARYFYAISDIKVRGRCKCN
LHATVCVYDNSKLTCECEHNTTGPDCGKCKKNYQGRPWSPGSYLPIPKGT
ANTCIPSISSIGNCECFGHSNRCSYIDLLNTVICVSCKHNTRGQHCELCR
LGYFRNASAQLDDENVCIECYCNPLGSIHDRCNGSGFCECKTGTTGPKCD
ECLPGNSWHYGCQPNVCDNELLHCQNGGTCHNNVRCLCPAAYTGILCEKL
RCEEAGSCGS NTNG1-isoform-3 aa 20-510
                                             SEQ ID NO: 3
HYDLCKTQIYTEEGKVWDYMACQPESTDMTKYLKVKLDPPDITCGDPPET
FCAMGNPYMCNNECDASTPELAHPPELMFDFEGRHPSTFWQSATWKEYPK
PLQVNITLSWSKTIELTDNIVITFESGRPDQMILEKSLDYGRTWQPYQYY
ATDCLDAFHMDPKSVKDLSQHTVLEIICTEEYSTGYTTNSKIIHFEIKDR
FAFFAGPRLRNMASLYGQLDTTKKLRDFFTVTDLRIRLLRPAVGEIFVDE
LHLARYFYAISDIKVRGRCKCNLHATVCVYDNSKLTCECEHNTTGPDCGK
CKKNYQGRPWSPGSYLPIPKGTANTCIPSISSIGNCECFGHSNRCSYIDL
LNTVICVSCKHNTRGQHCELCRLGYFRNASAQLDDENVCIECYCNPLGSI
HDRCNGSGFCECKTGTTGPKCDECLPGNSWHYGCQPNVCDNELLHCQNGG
TCHNNVRCLCPAAYTGILCEKLRCEEAGSCGS NTNG1 nucleic acid
                                             SEQ ID NO: 4
ATGTATTTGTCAAGATTCCTGTCGATTCATGCCCTTTGGGTTACGGTGTC
CTCAGTGATGCAGCCCTACCCTTTGGTTTGGGGACATTATGATTTGTGTA
AGACTCAGATTTACACGGAAGAAGGGAAAGTTTGGGATTACATGGCCTGC
CAGCCGGAATCCACGGACATGACAAAATATCTGAAAGTGAAACTCGATCC
TCCGGATATTACCTGTGGAGACCCTCCTGAGACGTTCTGTGCAATGGGCA
ATCCCTACATGTGCAATAATGAGTGTGATGCGAGTACCCCTGAGCTGGCA
CACCCCCCTGAGCTGATGTTTGATTTTGAAGGAAGACATCCCTCCACATT
TTGGCAGTCTGCCACTTGGAAGGAGTATCCCAAGCCTCTCCAGGTTAACA
TCACTCTGTCTTGGAGCAAAACCATTGAGCTAACAGACAACATAGTTATT
ACCTTTGAATCTGGGCGTCCAGACCAAATGATCCTGGAGAAGTCTCTCGA
TTATGGACGAACATGGCAGCCCTATCAGTATTATGCCACAGACTGCTTAG
ATGCTTTTCACATGGATCCTAAATCCGTGAAGGATTTATCACAGCATACG
GTCTTAGAAATCATTTGCACAGAAGAGTACTCAACAGGGTATACAACAAA
TAGCAA.AATAATCCACTTTGAAATCAAAGACAGGTTCGCGTTTTTTGCT
GGACCTCGCCTACGCAATATGGCTTCCCTCTACGGACAGCTGGATACAAC
CAAGAAACTCAGAGATTTCTTTACAGTCACAGACCTGAGGATAAGGCTGT
TAAGACCAGCCGTTGGGGAAATATTTGTAGATGAGCTACACTTGGCACGC
TACTTTTACGCGATCTCAGACATAAAGGTGCGAGGAAGGTGCAAGTGTAA
TCTCCATGCCACTGTATGTGTGTATGACAACAGCAAATTGACATGCGAAT
GTGAGCACAACACTACAGGTCCAGACTGTGGGAAATGCAAGAAGAATTAT
CAGGGCCGACCTTGGAGTCCAGGCTCCTATCTCCCCATCCCCAAAGGCAC
TGCAAATACCTGTATCCCCAGTATTTCCAGTATTGGTAATTGTGAATGCT
TCGGCCACTCCAATCGATGCAGTTATATCGATCTGCTAAATACAGTCATT
TGCGTGAGCTGTAAACACAACACTAGAGGGCAGCACTGTGAGTTATGCAG
GCTGGGCTACTTCAGAAATGCTTCTGCACAACTGGACGATGAGAATGTGT
GCATAGAGTGTTATTGTAACCCTTTGGGCTCAATCCATGATCGTTGTAAT
GGCTCAGGATTTTGTGAGTGTAAGACTGGAACAACAGGGCCTAAGTGTGA
TGAGTGTCTGCCGGGAAATTCCTGGCACTACGGCTGTCAACCGAATGTCT
GCGACAACGAGCTCCTGCACTGCCAGAACGGAGGGACGTGCCACAACAAC
GTGCGCTGCCTGTGCCCGGCCGCATACACGGGCATCCTCTGCGAGAAGCT
```

```
GCGGTGCGAGGAGGCTGGCAGCTGCGGCTCCGACTCTGGCCAGGGCGCGC
CCCCGCACGGCTCCCCAGCGCTGCTGCTGCTGACCACGCTGCTGGGAACC
GCCAGCCCCCTGGTGTTCTAG
```

NTNG1-isoform-1 amino acid

SEQ ID NO: 5

```
MYLSRFLSIHALWVTVSSVMQPYPLVWGHYDLCKTQIYTEEGKVWDYMAC
QPESTDMTKYLKVKLDPPDITCGDPPETFCAMGNPYMCNNECDASTPELA
HPPELMFDFEGRHPSTFWQSATWKEYPKPLQVNITLSWSKTIELTDNIVI
TFESGRPDQMILEKSLDYGRTWQPYQYYATDCLDAFHMDPKSVKDLSQHT
VLEIICTEEYSTGYTTNSKIIHFEIKDRFAFFAGPRLRNMASLYGQLDTT
KKLRDFFTVTDLRIRLLRPAVGEIFVDELHLARYFYAISDIKVRGRCKCN
LHATVCVYDNSKLTCECEHNTTGPDCGKCKKNYQGRPWSPGSYLPIPKGT
ANTCIPSISSIGTNVCDNELLHCQNGGTCHNNVRCLCPAAYTGILCEKLR
CEEAGSCGSDSGQGAPPHGSPALLLLTTLLGTASPLVF
```

NTNG1-isoform-2 amino acid

SEQ ID NO: 6

```
MYLSRFLSIHALVTVSSVMQPYPLVWGHYDLCKTQIYTEEGKVWDYMACQ
PESTDMTKYLKVKLDPPDITCGDPPETFCAMGNPYMCNNECDASTPELAH
PPELMFDFEGRHPSTFWQSATWKEYPKPLQVNITLSWSKTIELTDNIVIT
FESGRPDQMILEKSLDYGRTWQPYQYYATDCLDAFHMDPKSVKDLSQHTV
LEIICTEEYSTGYTTNSKIIHFEIKDRFAFFAGPRLRNMASLYGQLDTTK
KLRDFFTVTDLRIRLLRPAVGEIFVDELHLARYFYAISDIKVRGRCKCNL
HATVCVYDNSKLTCECEHNTTGPDCGKCKKNYQGRPWSPGSYLPIPKGTA
NTCIPSISSIGSK
```

NTNG1-isoform-4 amino acid

SEQ ID NO: 7

```
MYLSRFLSIHALWVTVSSVMQPYPLVWGHYDLCKTQIYTEEGKVWDYMAC
QPESTDMTKYLKVKLDPPDITCGDPPETFCAMGNPYMCNNECDASTPELA
HPPELMFDFEGRHPSTFWQSATWKEYPKPLQVNITLSWSKTIELTDNIVI
TFESGRPDQMILEKSLDYGRTWQPYQYYATDCLDAFHMDPKSVKDLSQHT
VLEIICTEEYSTGYTTNSKIIHFEIKDRFAFFAGPRLRNMASLYGQLDTT
KKLRDFFTVTDLRIRLLRPAVGEIFVDELHLARYFYAISDIKVRGRCKCN
LHATVCVYDNSKLTCECEHNTTGPDCGKCKKNYQGRPWSPGSYLPIPKGT
ANTCIPSISSIGNPPKFNRIWPNISSLEVSNPKQVAPKLALSTVSSVQVA
NHKRANVCDNELLHCQNGGTCHNNVRCLCPAAYTGILCEKLRCEEAGSCG
SDSGQGAPPHGSPALLLLTTLLGTASPLVF
```

NTNG1-isoform-5 amino acid

SEQ ID NO: 8

```
MYLSRFLSIHALWVTVSSVMQPYPLVWGHYDLCKTQIYTEEGKVWDYMAC
QPESTDMTKYLKVKLDPPDITCGDPPETFCAMGNPYMCNNECDASTPELA
HPPELMFDFEGRHPSTFWQSATWKEYPKPLQVNITLSWSKTIELTDNIVI
TFESGRPDQMILEKSLDYGRTWQPYQYYATDCLDAFHMDPKSVKDLSQHT
VLEIICTEEYSTGYTTNSKIIHFEIKDRFAFFAGPRLRNMASLYGQLDTT
KKLRDFFTVTDLRIRLLRPAVGEIFVDELHLARYFYAISDIKVRGRCKCN
LHATVCVYDNSKLTCECEHNTTGPDCGKCKKNYQGRPWSPGSYLPIPKGT
ANTCIPSISSIGNPPKFNRIWPNISSLEVSNPKQANVCDNELLHCQNGGT
CHNNVRCLCPAAYTGILCEKLRCEEAGSCGSDSGQGAPPHGSPALLLLTT
LLGTASPLVF
```

PLA2R1 amino acid

SEQ ID NO: 9

```
MLLSPSLLLLLLLGAPRGCAEGVAAALTPERLLEWQDKGIFVIQSESLKK
CIQAGKSVLTLENCKQANKHMLWKWVSNHGLFNIGGSGCLGLNFSAPEQP
LSLYECDSTLVSLRWRCNRKMITGPLQYSVQVAHDNTWASRKYIHKWISY
GSGGGDICEYLHKDLHTIKGNTHGMPCMFPFQYNHQWHHECTREGREDDL
LWCATTSRYERDEKWGFCPDPTSAEVGCDTSWEKDLNSHSCYQFNLLSSL
SWSEAHSSCQMQGGTLLSITDETEENFIREHMSSKTVEVWMGLNQLDEHA
GWQWSDGTPLNYLNWSPEVNFEPFVEDHCGTFSSFMPSAWRSRDCESTLP
YICKKYLNHIDHEIVEKDAWKYYATHCEPGWNPYNRNCYKLQKEEKTWHE
ALRSCQADNSAUDITSLAEVEFLVTLLGDENASETWIGLSSNKIPVSFEW
SNDSSVIFTNWHTLEPHIFPNRSQLCVSAEQSEGHWKVKNCEERLFYICK
KAGHVLSDAESGCQEGWERHGGFCYKIDTVLRSFDQASSGYYCPPALVTI
TNRFEQAFITSLISSVVKMKDSYFWIALQDQNDTGEYTWKPVGQKPEPVQ
YTHWNTHQPRYSGGCVAMRGRHPLGRWEVKHCRHFKAMSLCKQPVENQEK
AEYEERWPFHPCYLDWESEPGLASCFKVFHSEKVLMKRTWREAEAFCEEF
GAHLASFAHIEEENFVNELLHSKFNWTEERQFWIGFNKRNPLNAGSWEWS
DRTPVVSSFLDNTYFGEDARNCAVYKANKTLLPLHCGSKREWICKIPRDV
KPKIPFWYQYDVPWLFYQDAEYLFHTFASEWLNFEFVCSWLHSDLLTIHS
AHEQEFIHSKIKALSKYGASWWIGLQEERANDEFRWRDGTPVIYQNWDTG
RERTVNNQSQRCGFISSITGLWGSEECSVSMPSICKRKKVWLIEKKKDTP
KQHGTCPKWLYFNYKCLLLNIPKDPSSWKNWTHAQHFCAEEGGTLVAIES
EVEQAFITMNLFGQTTSVWIGLQNDDYETWLNGKPWYSNWSPFDIINIPS
HNTTEVQKHIPLCALLSSNPNFHFTGKWYFEDCGKEGYGFVCEKMQDTSG
HGVNTSDMYPMPNTLEYGNRTYKIINANMTWYAAIKTCLMHKAQLVSITD
QYHQSFLTVVLNRLGYAHWIGLFTTDNGLNFDWSDGTKSSFTFWKDEESS
LLGDCVFADSNGRWHSTACESFLQGAICHVPPETRQSEHPELCSETSIPW
IKFKSNCYSFSTVLDSMSFEAAHEFCKKEGSNLLTIKDEAENAFLLEELF
AFGSSVQMVWLNAQFDGNNETIKWFDGTPTDQSNWGIRKPDTDYFKPHHC
VALRIPEGLWQLSPCQEKKGFICKMEADIHTAEALPEKGPSHSIIPLAVV
LTLIVIVAICTLSFCIYKHNGGFFRRLAGFRNPYYPATNFSTVYLEENIL
ISDLEKSDQ
```

THSD7A ammo acid

SEQ ID NO: 10

```
MGLQARRWASGSRGAAGPRRGVLQLLPLPLPLPLLLLLLRPGAGRAAAQ
GEAEAPTLYLWKTGPWGRCMGDECGPGGIQTRAVWCAHVEGWTTLHTNCK
QAERPNNQQNCFKVCDWHKELYDWRLGPWNQCQPVISKSLEKPLECIKGE
EGIQVREIACIQKDKDIPAEDIICEYFEPKPLLEQACLIPCQQDCIVSEF
SAWSECSKTCGSGLQHRTRHVVAPPQFGGSGCPNLTEFQVCQSSPCEAEE
```

-continued

LRYSLHVGPWSTCSMPHSRQVRQARRRGKNKEREKDRSKGVKDPEARELI

KKKRNRNRQNRQENKYWDIQIGYQTREVMCINKTGKAADLSFCQQEKLPM

TFQSCVITKECQVSEWSEWSPCSKTCHDMVSPAGTRVRTRTIRQFPIGSE

KECPEFEEKEPCLSQGDGVVPCATYGWRTTEWTECRVDPLLSQQDKRRGN

QTALCGGGIQTREVYCVQANENLLSQLSTHKNKEASKPMDLKLCTGPIPN

TTQLCHIPCPTECEVSPWSAWGPCTYENCNDQQGKKGFKLRKRRITNEPT

GGSGVTGNCPHLLEAIPCEEPACYDWKAVRLGNCEPDNGKECGPGTQVQE

VCINSDGEEVDRQLCRDAIFPIPVACADAPCPKDCVLSTWSTWSSCSHTCS

GKTTEGKQIRARSILAYAGEEGGIRCPNSSALQEVRSCNEHPCTVYHWQT

GPWGQCIEDTSVSSFNTTTTWNGEASCSVGMQTRKVICVRVNVGQVGPKK

CPESLRPETVRPCLLPCKKDCIVTPYSDWTSCPSSCKEGDSSIRKQSRHR

VIIQLPANGGRDCTDPLYEEKACEAPQACQSYRWKTHKWRRCQLVPWSVQ

QDSPGAQEGCGPGRQARAITCRKQDGGQAGIHECLQYAGPVPALTQACQI

PCQDDCQLTSWSKFSSCNGDCGAVRTKRTLVGKSKKKEKCKNSHLYPLI

ETQYCPCDKYNAQPVGNWSDCILPEGKVEVLLGMKVQGDIKECGQGYRYQ

-continued

AMACYDQNGRLVETSRCNSGYIEEACIIPCPSDCKLSEWSNWSRCSKSCG

SGVKVRSKWLREKPYNGGRPCPKLDHVNQAQVYEVVPCHSDCNQYLWVTE

PWSICKVTFVNMRENCGEGVQTRKVRCMQNTADGPSEHVEDYLCDPEEMP

LGSRVCKLPCPEDCVISEWGPWTQCVLPCNQSSFRQRSADPIRQPADEGR

SCPNAVEKEPCNLNKNCYHYDYNVTDWSTCQLSEKAVCGNGIKTRMLDCV

RSDGKSVDLKYCEALGLEKNWQMNTSCMVECPVNCQLSDWSPWSECSQTC

GLTGKMIRRRTVTQPFQGDGRPCPSLMDQSKPCPVKPCYRWQYGQWSPCQ

VQEAQCGEGTRTRNISCVSDGSADDFSKVVDEEFCADIELIIDGNKNMVL

EESCSQPCPGDCYLKDWSSWSLCQLTCVNGEDLGFGGIQVRSRPVIIQEL

ENQHLCPEQMLETKSCYDGQCYEYKWMASAWKGSSRTVWCQRSDGINVTG

GCLVMSQPDADRSCNPPCSQPHSYCSETKTCHCEEGYTEVMSSNSTLEQC

TLIPVVVLPTMEDKRGDVKTSRAVHPTQPSSNPAGRGRTWFLQPFGPDGR

LKTWVYGVAAGAFVLLIFIVSMIYLACKKPKKPQRRQNNRLKPLTLAYDG

DADM

What is claimed:

1. An in vitro method, comprising:
   detecting one or more autoantibodies recognizing a human Netrin G1 (NTNG1) polypeptide or one or more anti-human NTNG1 antibody-binding fragments thereof in a biological sample obtained from a subject.

2. The in vitro method according to claim 1, wherein the in vitro method comprises:
   (i) contacting a biological sample obtained from the subject with the human Netrin G1 (NTNG1) polypeptide or one or more anti-human NTNG1 antibody-binding fragments thereof, and
   (ii) detecting any antigen-antibody complexes formed between the human NTNG1 polypeptide or one or more anti-human NTNG1 antibody-binding fragments thereof and anti-human NTNG1 autoantibodies in the biological sample.

3. The in vitro method according to claim 1, wherein detecting the antigen-antibody complexes between the human NTNG1 polypeptide or one or more anti-human NTNG1 antibody-binding fragments thereof and anti-human NTNG1 autoantibodies comprises determining the presence of anti-human NTNG1 autoantibodies.

4. An in vitro method of determining the effectiveness of treatment for membranous glomerulonephritis (MGN) in a subject, comprising:
   (i) treating a subject diagnosed with MGN by administering one or more immunosuppressive pharmaceutical substances;
   (ii) determining a level of anti-human Netrin G1 (NTNG1) autoantibodies in a first biological sample obtained from the subject at a first time-point; and
   (iii) determining a level of anti-human NTNG1 autoantibodies in a second biological sample obtained from the subject at a second time-point;
   wherein a decrease in the level of anti-human NTNG1 autoantibodies in the second time point compared to the first time point indicates that the treatment is effective; and/or an increase in the level of anti-human NTNG1 autoantibodies in the second time point compared to the first time point indicates that the treatment is not effective; and
   (iii) continuing the effective treatment of the subject diagnosed with MGN by administering the one or more immunosuppressive pharmaceutical substances.

5. The in vitro method according to claim 4, wherein determining the level of anti-human NTNG1 autoantibodies in the first biological sample or the second biological sample comprises contacting the first biological sample or the second biological sample obtained from the subject with a human Netrin G1 (NTNG1) polypeptide or one or more anti-human NTNG1 antibody-binding fragments thereof and detecting any antigen-antibody complexes formed between the human NTNG1 polypeptide or one or more anti-human NTNG1 antibody-binding fragments thereof and anti-human NTNG1 autoantibodies in the first biological sample or the second biological sample.

6. The in vitro method according to claim 1, wherein the biological sample is a blood sample.

7. An in vitro method for prognosis of membranous glomerulonephritis (MGN) in a subject, comprising:
   determining the expression level of human Netrin G1 (NTNG1) polypeptide or one or more anti-human NTNG1 antibody-binding fragments thereof in a biological sample obtained from said subject; and
   comparing said expression level to a reference expression level, wherein an increased expression level of human NTNG1 polypeptide or one or more anti-human NTNG1 antibody-binding fragments thereof compared to said reference expression level is indicative of MGN;
   wherein the expression level of the human NTNG1 polypeptide or one or more anti-human NTNG1 antibody binding fragment thereof in the biological sample is increased by at least 5%, compared to the reference expression level; and
   treating the MGN by administering one or more immunosuppressive pharmaceutical substances.

8. The in vitro method according to claim 7, wherein the reference expression level is determined by
   (i) determining the expression level of human NTNG1 polypeptide or one or more anti-human NTNG1 antibody-binding fragments thereof in biological samples obtained from a group of subjects without human NTNG1-associated MGN and/or a group of healthy subjects, and
   (ii) calculating a mean expression level of human NTNG1 polypeptide or one or more anti-human NTNG1 antibody-binding fragments thereof in said biological samples.

9. The in vitro method according to claim 7, wherein the biological sample is a renal biopsy sample.

10. The in vitro method according to claim 2, wherein the human NTNG1 polypeptide or one or more human NTNG1 antibody-binding fragments thereof are isolated and/or recombinant.

11. The in vitro method according to claim 2, wherein the human NTNG1 polypeptide or one or more anti-human NTNG1 antibody-binding fragments thereof are capable of binding to anti-human NTNG1 autoantibodies.

12. The in vitro method according to claim 2, wherein the human NTNG1 polypeptide comprises an amino acid sequence with at least 70% identity to the amino acid sequence according to SEQ ID NO: 1.

13. The in vitro method according to claim 2 wherein the anti-human NTNG1 antibody-binding fragment of the human NTNG1 polypeptide comprises at least 10 consecutive amino acids of the entire amino acid sequence of human NTNG1 according to SEQ ID NO: 1.

14. The in vitro method according to claim 2, wherein the human NTNG1 polypeptide or one or more anti-human NTNG1 antibody-binding fragments thereof are immobilized on a solid surface.

15. The in vitro method according to claim 14, wherein the solid surface is selected from the group consisting of an array, a microchip, a microplate, a bead, a resin, a membrane, and a column.

16. The in vitro method according to claim 6, wherein the blood sample is selected from one or more of the groups consisting of whole blood, plasma, serum, and capillary blood.

17. The in vitro method according to claim 1, wherein the human NTNG1 polypeptide or the one or more anti-human NTNG1 antibody-binding fragments thereof are isolated and/or recombinant.

* * * * *